US011896823B2

(12) United States Patent
Schwarz et al.

(10) Patent No.: US 11,896,823 B2
(45) Date of Patent: Feb. 13, 2024

(54) METHOD AND DEVICE FOR PELVIC FLOOR TISSUE TREATMENT

(71) Applicant: BTL Medical Technologies S.R.O., Prague (CZ)

(72) Inventors: Tomáš Schwarz, Prague (CZ); Lucia Jelinkova, Varin (SK); Jan Milichovsky, Cernovice (CZ)

(73) Assignee: BTL Healthcare Technologies a.s., Prague (CZ)

( * ) Notice: Subject to any disclaimer, the term of this patent is extended or adjusted under 35 U.S.C. 154(b) by 414 days.

(21) Appl. No.: 16/052,369

(22) Filed: Aug. 1, 2018

(65) Prior Publication Data

US 2018/0345012 A1 Dec. 6, 2018

Related U.S. Application Data

(63) Continuation-in-part of application No. 15/478,943, filed on Apr. 4, 2017, now Pat. No. 10,039,929.

(51) Int. Cl.
*A61N 1/36* (2006.01)
*A61N 1/40* (2006.01)
(Continued)

(52) U.S. Cl.
CPC .......... *A61N 1/36007* (2013.01); *A61N 1/40* (2013.01); *A61N 2/002* (2013.01); *A61N 2/004* (2013.01);
(Continued)

(58) Field of Classification Search
CPC .. A61N 1/36007; A61N 5/0603; A61N 2/002; A61N 1/40; A61N 1/403; A61N 2007/0043; A61N 7/02; A61N 2005/0611
See application file for complete search history.

(56) References Cited

U.S. PATENT DOCUMENTS 3,595,217 A 7/1971 Rheinfrank
3,915,151 A 10/1975 Kraus
(Continued)

FOREIGN PATENT DOCUMENTS

AU 2011233977 B2 2/2016
CN 2719341 U 8/2005
(Continued)

OTHER PUBLICATIONS

ABC Lasers, FemiLift Vaginal Tightening, 7 p., 2013.
(Continued)

*Primary Examiner* — Kaitlyn E Smith
*Assistant Examiner* — Annie L Shoulders
(74) *Attorney, Agent, or Firm* — Riverside Law LLP

(57) ABSTRACT

In methods and devices for treating a body canal or cavity, an internal applicator has an insertable part or section for insertion into the body canal or cavity (e.g. vagina or anal canal) and non-insertable part which may be detachable from a handle or second part of the device. The insertable part may include a plurality of energy delivery elements, optionally spaced apart in an array. During treatment the insertable part is positioned into or onto the body canal or cavity. The treatment may then proceed without additional movement of the insertable part. The energy delivery elements may be activated in predetermined order.

20 Claims, 14 Drawing Sheets

(51) Int. Cl.
*A61N 2/00* (2006.01)
*A61N 5/00* (2006.01)
*A61N 7/00* (2006.01)
*A61N 7/02* (2006.01)
*A61N 5/06* (2006.01)
*A61N 5/02* (2006.01)
*A61N 1/06* (2006.01)
*A61N 1/05* (2006.01)

(52) U.S. Cl.
CPC .......... *A61N 5/0603* (2013.01); *A61N 1/0512* (2013.01); *A61N 1/0524* (2013.01); *A61N 1/06* (2013.01); *A61N 5/022* (2013.01); *A61N 7/02* (2013.01); *A61N 2005/0611* (2013.01); *A61N 2007/0043* (2013.01)

(56) References Cited

U.S. PATENT DOCUMENTS

| | | |
|---|---|---|
| 4,326,529 A | 4/1982 | Doss |
| 4,381,007 A | 4/1983 | Doss |
| 4,665,898 A | 5/1987 | Costa |
| 4,785,807 A | 11/1988 | Blanch |
| 4,785,828 A | 11/1988 | Maurer |
| 4,907,589 A | 3/1990 | Cosman |
| 4,920,978 A | 5/1990 | Colvin |
| 4,976,709 A | 12/1990 | Sand |
| 4,993,413 A | 2/1991 | Mcleod |
| 5,010,895 A | 4/1991 | Maurer |
| 5,046,511 A | 9/1991 | Maurer |
| 5,085,626 A | 2/1992 | Frey |
| 5,143,063 A | 9/1992 | Fellner |
| 5,160,334 A | 11/1992 | Billings |
| 5,230,349 A | 7/1993 | Langberg |
| 5,242,440 A | 9/1993 | Shippert |
| 5,249,585 A | 10/1993 | Turner |
| 5,301,692 A | 4/1994 | Knowlton |
| 5,330,469 A | 7/1994 | Fleenor |
| 5,334,193 A | 8/1994 | Nardella |
| 5,348,554 A | 9/1994 | Imran |
| 5,401,233 A | 3/1995 | Erickson |
| 5,409,453 A | 4/1995 | Lundquist |
| 5,421,819 A | 6/1995 | Edwards |
| 5,423,329 A | 6/1995 | Ergas |
| 5,435,805 A | 7/1995 | Edwards |
| 5,439,467 A | 8/1995 | Benderev |
| 5,443,470 A | 8/1995 | Stern |
| 5,445,144 A | 8/1995 | Wodicka |
| 5,450,293 A | 9/1995 | Hoffman |
| 5,458,595 A | 10/1995 | Tadir |
| 5,458,596 A | 10/1995 | Lax |
| 5,469,857 A | 11/1995 | Laurent |
| 5,470,308 A | 11/1995 | Edwards |
| 5,470,309 A | 11/1995 | Edwards |
| 5,476,434 A | 12/1995 | Kalb |
| 5,484,400 A | 1/1996 | Edwards |
| 5,514,131 A | 5/1996 | Edwards |
| 5,531,676 A | 7/1996 | Edwards |
| 5,531,677 A | 7/1996 | Lundquist |
| 5,536,240 A | 7/1996 | Edwards |
| 5,542,915 A | 8/1996 | Edwards |
| 5,542,916 A | 8/1996 | Hirsch |
| 5,549,644 A | 8/1996 | Lundquist |
| 5,556,377 A | 9/1996 | Rosen |
| 5,562,717 A | 10/1996 | Tippey |
| 5,569,242 A | 10/1996 | Lax |
| 5,582,589 A | 12/1996 | Edwards |
| 5,591,125 A | 1/1997 | Edwards |
| 5,599,294 A | 2/1997 | Edwards |
| 5,599,295 A | 2/1997 | Rosen |
| 5,660,836 A | 8/1997 | Knowlton |
| 5,667,488 A | 9/1997 | Lundquist |
| 5,672,153 A | 9/1997 | Lax |
| 5,673,695 A | 10/1997 | Mcgee |
| 5,718,702 A | 2/1998 | Edwards |
| 5,720,718 A | 2/1998 | Rosen |
| 5,746,763 A | 5/1998 | Benderev |
| 5,755,753 A | 5/1998 | Knowlton |
| 5,765,567 A | 6/1998 | Knowlton |
| 5,766,124 A | 6/1998 | Polson |
| 5,769,778 A * | 6/1998 | Abrams ............. A61N 2/006 128/897 |
| 5,800,378 A | 9/1998 | Edwards |
| 5,824,076 A | 10/1998 | Knowlton |
| 5,836,990 A | 11/1998 | Li |
| 5,849,026 A | 12/1998 | Zhou |
| 5,871,524 A | 2/1999 | Knowlton |
| 5,919,219 A | 7/1999 | Knowlton |
| 5,937,863 A | 8/1999 | Knowlton |
| 5,947,891 A | 9/1999 | Morrison |
| 5,948,011 A | 9/1999 | Knowlton |
| 5,951,550 A | 9/1999 | Shirley |
| 5,954,717 A | 9/1999 | Behl |
| 5,957,920 A | 9/1999 | Baker |
| 5,964,727 A | 10/1999 | Edwards |
| 5,984,854 A | 11/1999 | Ishikawa |
| 6,002,968 A | 12/1999 | Edwards |
| 6,024,743 A | 2/2000 | Edwards |
| 6,035,238 A | 3/2000 | Ingle |
| 6,056,688 A | 5/2000 | Benderev |
| 6,056,744 A | 5/2000 | Edwards |
| 6,081,749 A | 6/2000 | Ingle |
| 6,110,099 A | 8/2000 | Benderev |
| 6,129,726 A | 10/2000 | Edwards |
| 6,132,365 A | 10/2000 | Sigurdsson |
| 6,155,966 A | 12/2000 | Parker |
| 6,156,060 A | 12/2000 | Roy |
| 6,179,769 B1 | 1/2001 | Ishikawa |
| 6,185,465 B1 * | 2/2001 | Mo ............. A61B 5/391 264/250 |
| 6,213,933 B1 | 4/2001 | Lin |
| 6,223,750 B1 | 5/2001 | Ishikawa |
| 6,241,753 B1 | 6/2001 | Knowlton |
| 6,277,116 B1 | 8/2001 | Utely |
| 6,311,090 B1 | 10/2001 | Knowlton |
| 6,350,276 B1 | 2/2002 | Knowlton |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,402,678 B1 | 6/2002 | Fischell |
| 6,405,090 B1 | 6/2002 | Knowlton |
| 6,413,255 B1 | 7/2002 | Stern |
| 6,416,504 B2 | 7/2002 | Mosel |
| 6,418,345 B1 | 7/2002 | Tepper |
| 6,419,653 B2 | 7/2002 | Edwards |
| 6,425,912 B1 | 7/2002 | Knowlton |
| 6,427,089 B1 | 7/2002 | Knowlton |
| 6,428,467 B1 | 8/2002 | Benderev |
| 6,428,538 B1 | 8/2002 | Blewett |
| 6,430,446 B1 | 8/2002 | Knowlton |
| 6,438,424 B1 | 8/2002 | Knowlton |
| 6,453,202 B1 | 9/2002 | Knowlton |
| 6,461,378 B1 | 10/2002 | Knowlton |
| 6,470,216 B1 | 10/2002 | Knowlton |
| 6,480,746 B1 | 11/2002 | Ingle |
| 6,482,204 B1 | 11/2002 | Lax |
| 6,527,694 B1 | 3/2003 | Ishikawa |
| 6,537,306 B1 | 3/2003 | Burdette |
| 6,569,078 B2 | 5/2003 | Ishikawa |
| 6,569,160 B1 | 5/2003 | Goldin |
| 6,572,639 B1 | 6/2003 | Ingle |
| 6,610,054 B1 | 8/2003 | Edwards |
| 6,659,936 B1 | 12/2003 | Furness |
| 6,749,624 B2 | 6/2004 | Knowlton |
| 6,814,712 B1 | 11/2004 | Edwards |
| 6,830,052 B2 | 12/2004 | Carter |
| 6,852,091 B2 | 2/2005 | Edwards |
| 6,875,209 B2 | 4/2005 | Zvuloni |
| 6,879,858 B1 | 4/2005 | Adams |
| 6,889,090 B2 | 5/2005 | Kreindel |
| 6,939,287 B1 | 9/2005 | Ardizzone |
| 7,022,105 B1 | 4/2006 | Edwards |

(56) References Cited

U.S. PATENT DOCUMENTS

| | | | |
|---|---|---|---|
| 7,022,121 | B2 | 4/2006 | Stern |
| 7,030,764 | B2 | 4/2006 | Smith |
| 7,141,049 | B2 | 11/2006 | Stern |
| 7,238,183 | B2 | 7/2007 | Kreindel |
| 7,294,127 | B2 | 11/2007 | Leung |
| 7,387,626 | B2 | 6/2008 | Edwards |
| 7,601,115 | B2 | 10/2009 | Riehl |
| 7,740,574 | B2 | 6/2010 | Pilla |
| 7,744,523 | B2 | 6/2010 | Epstein |
| 7,945,332 | B2 | 5/2011 | Schechter |
| 7,946,973 | B2 | 5/2011 | Peterchev |
| 7,998,053 | B2 | 8/2011 | Aho |
| 7,998,137 | B2 | 8/2011 | Elkins |
| 8,088,058 | B2 | 1/2012 | Juliana |
| 8,603,084 | B2 * | 12/2013 | Fish ............... A61B 5/1079 606/34 |
| 8,961,511 | B2 | 2/2015 | Parmer |
| 9,002,477 | B2 | 4/2015 | Burnett |
| 9,820,822 | B2 | 11/2017 | Cohen |
| 10,130,415 | B2 * | 11/2018 | Webster ............ A61B 18/1477 |
| 2001/0031906 | A1 | 10/2001 | Ishikawa |
| 2002/0049483 | A1 | 4/2002 | Knowlton |
| 2002/0058930 | A1 | 5/2002 | Furumoto |
| 2002/0062142 | A1 | 5/2002 | Knowlton |
| 2002/0120260 | A1 | 8/2002 | Morris |
| 2002/0151887 | A1 | 10/2002 | Stern |
| 2002/0156471 | A1 | 10/2002 | Stern |
| 2002/0183735 | A1 | 12/2002 | Edwards |
| 2003/0009201 | A1 | 1/2003 | Forsell |
| 2003/0097038 | A1 | 5/2003 | Presthus |
| 2003/0097162 | A1 | 5/2003 | Kreindel |
| 2003/0120326 | A1 | 6/2003 | Dietz |
| 2003/0130575 | A1 | 7/2003 | Desai |
| 2003/0130709 | A1 | 7/2003 | Haber |
| 2003/0139740 | A1 | 7/2003 | Kreindel |
| 2003/0139788 | A1 | 7/2003 | Eggers |
| 2003/0199866 | A1 | 10/2003 | Stern |
| 2003/0212393 | A1 | 11/2003 | Knowlton |
| 2003/0216728 | A1 | 11/2003 | Stern |
| 2003/0216729 | A1 | 11/2003 | Marchitto |
| 2003/0220635 | A1 | 11/2003 | Knowlton |
| 2003/0236487 | A1 | 12/2003 | Knowlton |
| 2004/0000316 | A1 | 1/2004 | Knowlton |
| 2004/0002704 | A1 | 1/2004 | Knowlton |
| 2004/0002705 | A1 | 1/2004 | Knowlton |
| 2004/0030332 | A1 | 2/2004 | Knowlton |
| 2004/0034346 | A1 | 2/2004 | Stern |
| 2004/0049251 | A1 | 3/2004 | Knowlton |
| 2004/0102824 | A1 | 5/2004 | Sharkey |
| 2004/0111087 | A1 | 6/2004 | Stern |
| 2004/0111136 | A1 | 6/2004 | Sharkey |
| 2004/0111137 | A1 | 6/2004 | Shankey |
| 2004/0127895 | A1 | 7/2004 | Flock |
| 2004/0172291 | A1 | 9/2004 | Knowlton |
| 2004/0186535 | A1 | 9/2004 | Knowlton |
| 2004/0206365 | A1 | 10/2004 | Knowlton |
| 2004/0210214 | A1 | 10/2004 | Knowlton |
| 2004/0210282 | A1 | 10/2004 | Flock |
| 2004/0236177 | A1 | 11/2004 | Matlock |
| 2005/0113877 | A1 | 5/2005 | Spinelli |
| 2005/0187599 | A1 | 8/2005 | Sharkey |
| 2005/0203399 | A1 * | 9/2005 | Vaezy ............... A61N 7/02 600/439 |
| 2005/0228371 | A1 | 10/2005 | West |
| 2006/0025837 | A1 | 2/2006 | Stern |
| 2006/0047331 | A1 | 3/2006 | Lax |
| 2006/0058780 | A1 | 3/2006 | Edwards |
| 2006/0152301 | A1 | 7/2006 | Rohwedder |
| 2006/0167533 | A1 | 7/2006 | Spraker |
| 2006/0187607 | A1 | 8/2006 | Mo |
| 2006/0205996 | A1 * | 9/2006 | Presthus ......... A61B 17/22004 600/29 |
| 2007/0050001 | A1 | 3/2007 | Luttich |
| 2007/0078502 | A1 | 4/2007 | Weber |
| 2007/0083247 | A1 | 4/2007 | Wyeth |
| 2007/0088413 | A1 | 4/2007 | Weber |
| 2007/0093807 | A1 | 4/2007 | Baxter |
| 2007/0106349 | A1 | 5/2007 | Karni |
| 2007/0233191 | A1 | 10/2007 | Parmer |
| 2008/0033374 | A1 | 2/2008 | Utley |
| 2008/0097422 | A1 | 4/2008 | Edwards |
| 2008/0125771 | A1 | 5/2008 | Lau |
| 2008/0132886 | A1 | 6/2008 | Cohen |
| 2008/0262287 | A1 | 10/2008 | Dussau |
| 2008/0281345 | A1 | 11/2008 | Wise |
| 2008/0306325 | A1 | 12/2008 | Burnett |
| 2009/0005631 | A1 | 1/2009 | Simenhaus |
| 2009/0076438 | A1 | 3/2009 | Edwards |
| 2010/0004644 | A1 | 1/2010 | Zipper |
| 2010/0004649 | A1 | 1/2010 | Baker |
| 2010/0087699 | A1 | 4/2010 | Peterchev |
| 2010/0100164 | A1 | 4/2010 | Johnson |
| 2010/0137737 | A1 | 6/2010 | Addington |
| 2010/0145138 | A1 | 6/2010 | Forsell |
| 2010/0145139 | A1 | 6/2010 | Forsell |
| 2010/0179372 | A1 | 7/2010 | Glassman |
| 2010/0331603 | A1 | 12/2010 | Szecsi |
| 2011/0015474 | A1 | 1/2011 | Forsell |
| 2011/0021863 | A1 | 1/2011 | Burnett |
| 2011/0043297 | A1 | 2/2011 | Stevenson |
| 2011/0210274 | A1 | 9/2011 | Kempe |
| 2011/0263925 | A1 | 10/2011 | Bratton |
| 2012/0016239 | A1 | 1/2012 | Barthe |
| 2012/0053396 | A1 | 3/2012 | Deegan |
| 2012/0053449 | A1 | 3/2012 | Moses |
| 2012/0065494 | A1 * | 3/2012 | Gertner ............... A61B 8/06 601/2 |
| 2012/0136407 | A1 | 5/2012 | Presthus |
| 2012/0197251 | A1 | 8/2012 | Edwards |
| 2012/0239055 | A1 | 9/2012 | Spector |
| 2012/0253107 | A1 | 10/2012 | Gindele |
| 2012/0296199 | A1 | 11/2012 | Kim |
| 2013/0030239 | A1 | 1/2013 | Weyh |
| 2013/0116677 | A1 | 5/2013 | Eskuri |
| 2013/0123568 | A1 | 5/2013 | Hamilton |
| 2013/0158634 | A1 | 6/2013 | Ron Edoute |
| 2013/0197505 | A1 | 8/2013 | Edwards |
| 2013/0211400 | A1 | 8/2013 | Qin |
| 2013/0238061 | A1 | 9/2013 | Ron Edoute |
| 2013/0245728 | A1 | 9/2013 | Galen |
| 2013/0253509 | A1 | 9/2013 | Edwards |
| 2013/0317281 | A1 | 11/2013 | Schneider |
| 2014/0039491 | A1 * | 2/2014 | Bakos ............. A61B 18/1492 606/41 |
| 2014/0046423 | A1 | 2/2014 | Rajguru |
| 2014/0081257 | A1 | 3/2014 | Ghoniem |
| 2014/0148878 | A1 | 5/2014 | Khatri |
| 2014/0200480 | A1 | 7/2014 | West |
| 2014/0221996 | A1 | 8/2014 | West |
| 2014/0330174 | A1 | 11/2014 | Warlick |
| 2015/0011990 | A1 | 1/2015 | Qin |
| 2015/0025299 | A1 | 1/2015 | Ron Edoute |
| 2015/0123661 | A1 | 5/2015 | Yui |
| 2015/0133717 | A1 | 5/2015 | Ghiron |
| 2015/0148701 | A1 | 5/2015 | Bek |
| 2015/0157873 | A1 | 6/2015 | Sokolowski |
| 2015/0165241 | A1 * | 6/2015 | Burdette ............. A61B 8/0841 601/3 |
| 2015/0202467 | A1 | 7/2015 | Diederich |
| 2015/0257695 | A1 | 9/2015 | Addington |
| 2015/0282763 | A1 * | 10/2015 | Rosenshein ........ A61B 5/4331 600/301 |
| 2015/0328475 | A1 | 11/2015 | Kim |
| 2015/0366747 | A1 | 12/2015 | Lei |
| 2015/0367141 | A1 | 12/2015 | Goetz |
| 2016/0022357 | A1 | 1/2016 | Utley |
| 2016/0051827 | A1 | 2/2016 | Ron Edoute |
| 2016/0074109 | A1 | 3/2016 | West |
| 2016/0101288 | A1 | 4/2016 | Fraga Da Silva |
| 2016/0106465 | A1 * | 4/2016 | Richey ............. A61B 17/4241 600/37 |
| 2016/0220302 | A1 | 8/2016 | Zarins |
| 2016/0263389 | A1 | 9/2016 | Alinsod |
| 2017/0065222 | A1 | 3/2017 | Egorov |

(56) References Cited

U.S. PATENT DOCUMENTS

| | | | |
|---|---|---|---|
| 2017/0071651 A1* | 3/2017 | Allan | A61B 18/20 |
| 2017/0105784 A1* | 4/2017 | Su | A61B 18/1492 |
| 2017/0179631 A1* | 6/2017 | Feldchtein | H01R 13/193 |
| 2017/0209707 A1* | 7/2017 | Casalino | A61N 1/06 |
| 2017/0215936 A1* | 8/2017 | Wallace | A61B 18/14 |
| 2018/0000533 A1* | 1/2018 | Boll | A61B 18/1206 |
| 2018/0036554 A1* | 2/2018 | Krespi | A61N 5/022 |
| 2018/0064937 A1* | 3/2018 | Lischinsky | A61F 5/41 |
| 2020/0086110 A1* | 3/2020 | Karsdon | A61N 1/05 |
| 2020/0139138 A1* | 5/2020 | Sit | A61N 1/378 |
| 2021/0161591 A1* | 6/2021 | Kreindel | A61B 18/1485 |

FOREIGN PATENT DOCUMENTS

| | | |
|---|---|---|
| CN | 202724094 U | 2/2013 |
| CN | 202751492 U | 2/2013 |
| CN | 202802519 U | 3/2013 |
| CN | 202859437 U | 4/2013 |
| CN | 202859438 U | 4/2013 |
| CN | 202859916 U | 4/2013 |
| CN | 103300961 A | 9/2013 |
| CN | 103301568 A | 9/2013 |
| CN | 103301573 A | 9/2013 |
| CN | 204072697 U | 1/2015 |
| CN | 204092183 U | 1/2015 |
| CN | 104587598 A | 5/2015 |
| CN | 204684479 U | 10/2015 |
| CN | 106310530 A | 1/2017 |
| CN | 206252732 U | 6/2017 |
| CN | 107510889 A | 2/2019 |
| EP | 0209246 A1 | 1/1987 |
| EP | 0291569 | 11/1988 |
| EP | 0938910 A2 | 9/1999 |
| EP | 1414516 | 5/2004 |
| EP | 2676700 A2 | 12/2013 |
| EP | 3195898 A1 | 7/2017 |
| ES | 2147518 A1 | 9/2000 |
| FR | 2767481 A1 | 2/1999 |
| GB | 2360460 | 9/2001 |
| JP | H05269144 | 10/1993 |
| JP | H09122141 | 5/1997 |
| JP | H11504828 | 5/1999 |
| JP | 2002238919 | 8/2002 |
| JP | 2003503118 | 1/2003 |
| JP | 2006187668 | 7/2006 |
| KR | 20020068565 A | 8/2002 |
| KR | 200374103 Y1 | 1/2005 |
| KR | 100816847 B1 | 3/2008 |
| KR | 101039636 B1 | 6/2011 |
| KR | 20110061072 A | 5/2012 |
| KR | 20130123147 A | 3/2014 |
| KR | 20140052839 A | 5/2014 |
| KR | 20160063784 A | 6/2016 |
| KR | 20160065578 A | 6/2016 |
| RU | 2146957 | 3/2000 |
| RU | 2163822 | 3/2001 |
| RU | 2192903 C2 | 11/2002 |
| RU | 2268077 | 1/2006 |
| RU | 2557416 C1 | 7/2015 |
| WO | 1993017757 A1 | 9/1993 |
| WO | 1995010981 | 4/1995 |
| WO | 1995022378 A1 | 8/1995 |
| WO | 9601597 A3 | 3/1996 |
| WO | 9620753 A1 | 7/1996 |
| WO | 1996022739 | 8/1996 |
| WO | 9700639 A2 | 1/1997 |
| WO | 1997018857 A1 | 5/1997 |
| WO | 1997034534 | 9/1997 |
| WO | 1997036641 A1 | 10/1997 |
| WO | 1997036644 A1 | 10/1997 |
| WO | 1997048446 A1 | 12/1997 |
| WO | 1998011834 A1 | 3/1998 |
| WO | 1998019613 A1 | 5/1998 |
| WO | 1998034677 A1 | 8/1998 |
| WO | 1999008614 A1 | 2/1999 |
| WO | 1999019024 A1 | 4/1999 |
| WO | 1999027991 A1 | 6/1999 |
| WO | 1999035983 A1 | 7/1999 |
| WO | 1999035986 A1 | 7/1999 |
| WO | 9942044 A1 | 8/1999 |
| WO | 1999043263 A1 | 9/1999 |
| WO | 1999044522 A1 | 9/1999 |
| WO | 1999048438 A1 | 9/1999 |
| WO | 1999053853 | 10/1999 |
| WO | 1999066844 A1 | 12/1999 |
| WO | 0001320 A2 | 1/2000 |
| WO | 2000006035 A1 | 2/2000 |
| WO | 2000006047 A1 | 2/2000 |
| WO | 2000006061 A1 | 2/2000 |
| WO | 2000006246 A1 | 2/2000 |
| WO | 2000015300 A1 | 3/2000 |
| WO | 2000018314 A1 | 4/2000 |
| WO | 2000019939 A1 | 4/2000 |
| WO | 2000019940 A1 | 4/2000 |
| WO | 2000023030 A1 | 4/2000 |
| WO | 2000023127 A1 | 4/2000 |
| WO | 2000028939 A2 | 5/2000 |
| WO | 2000049947 A1 | 8/2000 |
| WO | 2000059393 A1 | 10/2000 |
| WO | 2000062696 A1 | 10/2000 |
| WO | 2000066006 A1 | 11/2000 |
| WO | 2000066013 A1 | 11/2000 |
| WO | 2000066015 A1 | 11/2000 |
| WO | 2000066016 A1 | 11/2000 |
| WO | 2000066017 A1 | 11/2000 |
| WO | 2000066018 A1 | 11/2000 |
| WO | 2000069376 A1 | 11/2000 |
| WO | 2000078241 A1 | 12/2000 |
| WO | 2000079497 A1 | 12/2000 |
| WO | 2001005318 A1 | 1/2001 |
| WO | 0117453 A2 | 3/2001 |
| WO | 0118616 A2 | 3/2001 |
| WO | 2001017469 A1 | 3/2001 |
| WO | 2001022897 A1 | 4/2001 |
| WO | 2001037732 A1 | 5/2001 |
| WO | 0145486 A2 | 6/2001 |
| WO | 0147433 A2 | 7/2001 |
| WO | 0150833 A2 | 7/2001 |
| WO | 2001052930 A1 | 7/2001 |
| WO | 2001058388 A1 | 8/2001 |
| WO | 0168015 A1 | 9/2001 |
| WO | 2001080723 A2 | 11/2001 |
| WO | 2002025675 A1 | 3/2002 |
| WO | 2002028475 A1 | 4/2002 |
| WO | 2002034328 A1 | 5/2002 |
| WO | 2002065975 A1 | 8/2002 |
| WO | 03002186 | 1/2003 |
| WO | 03002186 A2 | 1/2003 |
| WO | 03002187 A2 | 1/2003 |
| WO | 2003011158 | 2/2003 |
| WO | 2003043536 A1 | 5/2003 |
| WO | 2003053521 A1 | 7/2003 |
| WO | 2003065908 | 8/2003 |
| WO | 03077742 A2 | 9/2003 |
| WO | 2003079931 A1 | 10/2003 |
| WO | 2003090863 A1 | 11/2003 |
| WO | 2004010843 A2 | 2/2004 |
| WO | 2004012578 A2 | 2/2004 |
| WO | 2004025044 A2 | 3/2004 |
| WO | 2004033040 A1 | 4/2004 |
| WO | 2004043543 | 5/2004 |
| WO | 2004047914 A1 | 6/2004 |
| WO | 2004064599 A2 | 8/2004 |
| WO | 2005020931 A2 | 3/2005 |
| WO | 2005051329 A2 | 6/2005 |
| WO | 2005074648 A2 | 8/2005 |
| WO | 2005074649 A2 | 8/2005 |
| WO | 2005086739 A2 | 9/2005 |
| WO | 2005099369 A2 | 10/2005 |
| WO | 2005122727 A2 | 12/2005 |
| WO | 2005123184 A2 | 12/2005 |

(56) References Cited

FOREIGN PATENT DOCUMENTS

| | | |
|---|---|---|
| WO | 2006007284 A2 | 1/2006 |
| WO | 2006033067 | 3/2006 |
| WO | 2006034357 | 3/2006 |
| WO | 2006105121 | 10/2006 |
| WO | 2007025294 A2 | 3/2007 |
| WO | 2007080578 A2 | 7/2007 |
| WO | 2007106520 A2 | 9/2007 |
| WO | 2007106680 A2 | 9/2007 |
| WO | 2007136266 A1 | 11/2007 |
| WO | 2007145913 A1 | 12/2007 |
| WO | 2008031159 A1 | 3/2008 |
| WO | 2008046050 A2 | 4/2008 |
| WO | 2008049084 A2 | 4/2008 |
| WO | 2008058145 A2 | 5/2008 |
| WO | 2008067304 A2 | 6/2008 |
| WO | 2008067317 A2 | 6/2008 |
| WO | 2009048379 A2 | 4/2009 |
| WO | 2009128940 A1 | 10/2009 |
| WO | 2010007419 A1 | 1/2010 |
| WO | 2010040556 A2 | 4/2010 |
| WO | 2010042045 A1 | 4/2010 |
| WO | 2010042046 A1 | 4/2010 |
| WO | 2010048334 A1 | 4/2010 |
| WO | 2010048335 A1 | 4/2010 |
| WO | 2010053700 A1 | 5/2010 |
| WO | 2011011748 A1 | 1/2011 |
| WO | 2011034986 A2 | 3/2011 |
| WO | 2011037621 A2 | 3/2011 |
| WO | 2011050252 A1 | 4/2011 |
| WO | 2011096006 A1 | 8/2011 |
| WO | 2011112248 A2 | 9/2011 |
| WO | 2011123860 A1 | 10/2011 |
| WO | 2011133431 A2 | 10/2011 |
| WO | 2011158999 A1 | 12/2011 |
| WO | 2012088159 A2 | 6/2012 |
| WO | 2012092508 A2 | 7/2012 |
| WO | 2012095653 A1 | 7/2012 |
| WO | 2013016588 A1 | 1/2013 |
| WO | 2013016590 A1 | 1/2013 |
| WO | 2013050994 A1 | 4/2013 |
| WO | 2013082006 A1 | 6/2013 |
| WO | 2013096913 A2 | 6/2013 |
| WO | 2013096916 A2 | 6/2013 |
| WO | 2013096919 A1 | 6/2013 |
| WO | 2013096920 A1 | 6/2013 |
| WO | 2013096922 A1 | 6/2013 |
| WO | 2013138658 A1 | 9/2013 |
| WO | 2013138718 A1 | 9/2013 |
| WO | 2013160772 A2 | 10/2013 |
| WO | 2013184798 A1 | 12/2013 |
| WO | 2013185121 A1 | 12/2013 |
| WO | 2013188640 A1 | 12/2013 |
| WO | 2015014811 A1 | 2/2015 |
| WO | 2015058128 A1 | 4/2015 |
| WO | 2015059120 A1 | 4/2015 |
| WO | 2015070242 A2 | 5/2015 |
| WO | 2015079322 A2 | 6/2015 |
| WO | 2015116512 A1 | 8/2015 |
| WO | 2015179837 A1 | 11/2015 |
| WO | 2015187615 A1 | 12/2015 |
| WO | 2015192694 A1 | 12/2015 |
| WO | 2016098995 A2 | 6/2016 |
| WO | 2016123608 A2 | 8/2016 |
| WO | 2016127130 A1 | 8/2016 |
| WO | 2016198955 A2 | 12/2016 |
| WO | 2017042737 A1 | 3/2017 |
| WO | 2017070372 A1 | 4/2017 |
| WO | 2017103923 A1 | 6/2017 |
| WO | 2017147399 A1 | 8/2017 |
| WO | 2018006086 A1 | 1/2018 |
| WO | 2018008023 A1 | 1/2018 |
| WO | 2018144615 A1 | 8/2018 |
| WO | 2018164676 A1 | 9/2018 |
| WO | 2018213754 A1 | 11/2018 |

OTHER PUBLICATIONS

Alma Lasers, Femilift Brochure, 2 p., 2013.
Alma Lasers, Pixel CO2 Operator's Manual, Apr. 2014, 161 pages.
Alma Lasers, The Non-Invasive Laser Solution for Vaginal Tightening and Stress Urinary Incontinence Reduction, 6 p., 2015.
Bader, Alexandros, Case Study non invasive treatment of SUI with CO2, Mar. 2014, 6 pages.
Coad et al., RF Treatment of the Introitus in a Sheep Model: Parameter Optimization to Improve Vaginal Laxity, Apr. 2012, 1 page.
Cynosure, Femilift vs. MonaLisa Touch, Competitive Product Comparison, 2 p., Oct. 2015.
Cynosure, Fotona Smooth SP vs. MonaLisa Touch, Competitive Product Comparison, 3 p., Nov. 2015.
Cynosure, MonaLisa Touch Clincal Reference Guide (2016), 49 pages.
Cynosure, THERMIva vs. MonaLisa Touch, Competitive Product Comparison, 2 p., Oct. 2015.
Deka Smartxide Touch 501 (k) Letter, Food and Drug Administration, Nov. 17, 2017, 5 pages.
Deka, MonaLisa Touch Brochure, 8 p., Oct. 2013.
Fistonic et al, Minimally invasive laser procedure for early stages of stress urinary incontinence (SUI) J Laser and Health Academy, vol. 2012, No. 1, pp. 67-74 (2012).
Foley et al, Non-Invasive Labial Correction: Improvement of Labial Skin Laxity and Texture Using Viora's V-ST Handpiece Utilizing CORE™ Technology, Viora, 2014, 3 pages.
Fotana d.d., Uživatelská Příručka, 2014, 22 pages.
Fotona d.d., Aplikační Manuál, Er:YAG a Nd:YAG v gynekologii, Dec. 2014, 59 pages.
Fotona d.d., Dynamis/Spectro Operator Manual, Sep. 2014, 111 pages.
Fotona Dynamis Pro Family 510(k) Letter, Food and Drug Administration, Apr. 9, 2015, 10 pages.
FotonaSmooth Brochure, 6p., Dec. 2012, 6 pages.
Frentzen, J., Non-Surgical Feminine Rejuvenation Presents Significant Practice Growth Opportunity, The Aesthetic Guide, Nov. 2014, 5 pages.
Gaviria et al, Laser Vaginal Tightening (LVT)—evaluation of a novel noninvasive laser treatment for vaginal relaxation syndrome, J Laser and Health Academy, vol. 2012, No. 1, pp. 59-66 (2012).
Genityte Brochure, 2 p, Mar. 2015.
Herbst et al., Radiofrequency Treatment of Vaginal Laxity—Nonsurgical Vaginal Tightening, Aug. 2012, 16 pages.
ICS Presentation, A Cross-Sectional Survey to Assess the Symptoms Associated with and Prevalence of vaginal Laxity, Aug. 2012, 22 pages.
Key, D., A Preliminary Study of a Transdermal Radiofrequency Device for Body Slimming, Journal of Drugs in Dermatology, 14:11, Nov. 2015, 7 pages.
Kingsberg, et al., Vaginal Laxity After Childbirth: Qualitative Survey Of Women's Perceptions, Effect On Changes In Self-Image And Sexual Relationships, Aug. 2012, 1 page.
Krychman, M, Effect of Single-Treatment, Surface-Cooled Radiofrequency Therapy on Vaginal Laxity and Female Sexual Function: The VIVEVE I Randomized Controlled Trial, J Sex Med 2017; 14:215-225.
Krychman, M, The Viveve System is a Non-Invasive Treatment for Vaginal Introital Laxity that Improve Sexual Function in Adult Female Subjects, Mar. 2014, 21 pages.
Laser Vaginal Rejuvenation with Alma Pixel CO2, Interview with Dr. Femopase, 4 p., 2013.
Lukes et al., OB/GYNs' Attitudes and Perceptions Regarding Sexual Health of Patients After Delivery, ISSWSH Poster, Aug. 2012, 1 page.
Millheiser et al., Laxity of the Vaginal Introitus: An Infrequently Discussed Medical Consequence of Vaginal Deliveries, Poster, Aug. 2012, 1 page.
Millheiser et al, Radiofrequency Treatment of Vaginal Laxity after Vaginal Delivery: Nonsurgical Vaginal Tightening, J Sex Med., 2010; 7:3088-3095.

(56) References Cited

OTHER PUBLICATIONS

Millheiser et al., A Cross-Sectional Survey to Assess the Prevalence and Symptoms Associated with Laxity of the Vaginal Introitus, Aug. 23, 2010, 3 pages.

Millheiser et al., Cross-sectional Survey of Sexual Health and Vaginal Laxity Following Vaginal Delivery, ISSM Poster, Aug. 2012, 1 page.

Pelosi, M, Femilift Laser Vaginal Tightening: A Star is Born, Realself.com, Mar. 2, 2015, 3 pages.

Petrou, I, Multidisciplinary Laser Explores, New Therapeutic Frontiers, The Asian Aesthetic Guide, vol. 4 (2013), 1 page.

Ronconi et al., MonaLisa Touch: The Latest Frontier in the Treatment of Vaginal Atrophy, 105 p., Nov. 2012.

Salvatore et al, A 12-week treatment with fractional CO2 laser for vulvovaginal atrophy: A pilot study, Climacteric, Mar. 2014, 8 pages.

Sekiguchi, et al., a Prospective Longitudinal Single-Arm Study of Low-Energy Radiofrequency (RF) Applied to the Vaginal Introitus to Improve Vaginal Laxity and Sexual Satisfaction in Female Patients: Interim Results at Three-Months, Yokohama Motomachi Women's Clinic LUNA, Aug. 2012, 5 pages.

ThermiAesthetics ThermiRF Operators Manual, 39 p., Dec. 2013.

ThermiRF Introduction, 143 p., Apr. 2016.

Viora ReVive Brochure, 2 p., Jan. 2014.

Viveve Brochure, 2 p., Oct. 2017.

Viveve System Instructions for Use, 4 p., Feb. 2017.

Viveve System Technical User's Manual, 51 p., Nov. 2017.

Viveve, Geneveve Brochure, 2 p., 2016.

Vizintin et al., Novel Minimally Invasive VSP Er:YAG Laser Treatments in Gynecology, J Laser and Health Academy, vol. 2012, No. 1, pp. 46-58 (2012).

Vos et al., Non-ablative hyperthermic mesenchymal regenaration: A proposed mechanism of action based on the Viveve model, Energy-based Treatment of Tissue and Assessment VI, Proc. of SPIE vol. 7901, 2011, 8 pages.

GymnaUniphy, N.V., Phyaction C User Manual, 94 pp, 2004.

GymnaUniphy, N. V., COMBI 200L User Manual, 100 pp, 2004.

Lenihan, J.,Comparison of the quality of life after nonsurgical radiofrequency energy tissue micro-remodeling in premenopausal and postmenopausal women with moderate-to-severe stress urinary incontinence, Am. J. Obstetrics and Gynecology, 192, 1995-2001 (2005).

Lin, V.W., et al., "Functional Magnetic Stimulation: A New Modality for Enhancing Systemic Fibrinolysis," Archives of Physical Medicine and Rehabilitation 80(5):545-550, W.B. Saunders, United States (May 1999).

U.S. Patent and Trademark Office, Non-final Office Action issued in U.S. Appl. No. 15/344,811 dated Mar. 28, 2017.

* cited by examiner

METHOD AND DEVICE FOR PELVIC FLOOR TISSUE TREATMENT

CROSS-REFERENCE TO RELATED APPLICATION(S)

This Application is a Continuation-in-part of U.S. patent application Ser. No. 15/478,943 filed Apr. 4, 2017, now pending, which is incorporated by reference herein in its entirety.

FIELD OF THE INVENTION

This invention relates to apparatus and methods for genital rejuvenation, remodeling, treatment of sexual dysfunction, gynecological treatment and treatment of organs or tissues located in or near the pelvic floor.

BACKGROUND

The pelvic floor is formed in a bowl-like structure and contains tissues and organs including the male or female genitals, urethra, bladder or rectum. Pelvic floor organs and tissue include cavities. Dysfunction of the pelvic floor may be demonstrated, for example, by incontinence, rectal/anal canal prolapse, vaginal prolapse, chronic pain, functional constipation, infections and inflammations. It may be also demonstrated by sexual problems like erectile, ejaculatory and orgasmic dysfunction or dyspareunia. The muscle contraction may be responsible for some functions of the pelvic floor, while the connective tissue (including collagen, elastin, fibronectin, laminins, glycoproteins, proteoglycans and/or matricellular proteins) provides structural support for the pelvic floor organs.

The female genital tissue contains the vulva and vagina. The vulva is an external, visible part of the female genital tissue including the mons pubis, labia majora, labia minora, hymen, clitoris, vaginal opening and urethral orifice. Perineum is a tissue part located below genital tissue. The labia minora and vaginal opening forms cavity called vulvar vestibule. While the mons pubis, labia majora and perineum have a fully keratinized, stratified squamous epithelium, the degree of keratinization of the labia minora declines from the outer surface to the inner surface. The mons pubis and labia majora include fatty tissue and loose connective tissue. The labia minora has mainly connective tissue and some smooth muscle fibres making it an erectile structure. The clitoris contains erectile tissue and connective tissue. The human vagina is a canal composed of four layers, the outermost is the epithelium, below which extends a subepithelial layer called the lamina propria, the muscularis and in the innermost is the adventitia.

There are few therapeutic approaches to treat female genital tissue. For example, in case of vaginal prolapse or rejuvenation, surgery of the pelvic floor or unnecessary tissue may be performed. Such method is painful and requires invasive treatment of sensitive areas. Another approach, used for vaginal and vulvar rejuvenation, utilizes the electromagnetic energy for denaturation of existing tissue to induce the deposition of a newly synthetized tissue. However, this method requires the operator to move the applicator over treated area, which may cause discomfort for the patient. The shape of already used applicator is also a limitation of such methods.

This method includes delivering only one type of energy and requires uncomfortably long and repeated treatment sessions. It may also not provide sufficient treatment without the risk of relapse.

Another limitation of known treatments is the inappropriate shape of applicators for delivering the energy. Such applicators deliver energy only to the part of the tissue. Therefore the biological effect is induced only in the affected portion of the tissue. Treatment may require repeated repositioning and continuous movement of the applicator in order to treat the intended tissue part. Moreover, the shape and technical solution of such applicators does not allow their adaptability to the patient. The medical professional and the patient may therefore face problems during the treatment related to the rigid and fixed construction of the applicator and the shape of the treated pelvic floor tissue. Such problems may lead to ineffective, uncomfortable and even painful treatment.

Also, the existing therapeutic approaches for the treatment of other parts of the pelvic floor, for example the rectum, anus and the perineum, use invasive surgical methods or have similar disadvantages as described above. In particular, the treatment of fecal incontinence is mainly targeted to the muscle structure of the sphincters. Presently, this approach uses invasive electrodes to stimulate the muscle and therefore it may be painful for the patient. The treated tissue may become more sensitive and it may lead to problems after treatment.

Furthermore, the currently used methods for treating pelvic floor tissues and organs are contact or even invasive methods and may cause discomfort to the patient by the necessity of uncovering an intimate part of the body. Another disadvantage is discomfort caused by the touching of the intimate parts of the body by medical professional. As a result, patients may avoid treatment of the pelvic floor tissue, which may lead to worsening of their condition.

There is a need for new methods and devices for treatment of pelvic floor tissues and organs.

SUMMARY OF THE INVENTION

The present methods and devices may be used for treatment of tissue by application of energy. Energy may be delivered by one or more energy delivery elements.

Devices and methods apply combination of at least two different types of energy. Such combination of types of energy may provide faster and more consistent treatment of the tissue with the long lasting results.

A first type of energy may be replaced by second type of energy. Alternatively, the first and second type of energies may be supplied simultaneously by one or more applicators. The energy may be any kind of electromagnetic energy (e.g. light, radiofrequency energy and/or microwave energy); mechanical energy (e.g. acoustic wave, ultrasound wave or shock wave), electric, magnetic energy and/or plasma. Treatment may require different energy types, depth, power and/or focus.

The applicator may have one or more detachable parts. A detachable part may include one or more energy delivery elements or no energy delivery elements.

Alternatively, the detachable part may include at least two energy delivery elements delivering different types of energy. Detachable parts may be combined and/or assembled to create an applicator of any size, shape, length, width, type of energy and/or elasticity. Therefore, the user may change the applicator by attaching at least one detachable part to the applicator.

The method and device may be used for treatment of many health issues of the pelvic floor tissue for e.g. maintaining of stability of vaginal environment, vaginal laxity or treating of issues associated with anal and rectum. Furthermore, the method and device may be also used for treatment of erectile issues related to the penis, mons pubis and other tissues.

Internal and external applicators may be used separately or together. The applicator may be implemented in garments and/or may be worn on the body during normal activities. A system may include expandable elements ensuring the delivery of the energy adjacent to the tissue.

Energy may be delivered to the patient in a self-operated manner i.e. operated without the continuous supervision and/or manual action of an operator. This saves time and cost, because the operator may simultaneously treat more than one patient. A self-operated device containing a self-operated applicator may minimize and/or prevent mistakes of a human operator, e.g. burning of the tissue. The device may be also incorporated into a supporting structure, e.g. a chair or bed.

Optionally, the device and method may include application of the energy by the applicator with direct contact, indirect contact or no contact with the tissue. In case of no contact, the applicator may be spaced apart from the tissue by a gap. This configuration may be used for treatment without need of undressing and touching the patient.

Glossary

The term "energy" means any type of energy or field applied by the device. It may be electromagnetic energy which may be light, radiofrequency energy and/or microwave energy, mechanical energy which may be ultrasound energy and/or shock wave energy, magnetic energy, vibrational energy, electric energy, thermal energy and/or plasma. The energy may be unfocused and/or focused to one or more one areas. The energy may include coherent and/or non-coherent energy.

The term "direct contact" means any contact of the applicator of the device with the tissue.

The term "indirect contact" means any contact of the applicator with the tissue through spacing object.

The term "no contact" means the applicator is spaced apart from the tissue by a gap.

The term "biological effect" means any one or more of: a cell death, apoptosis, necrosis, analgesic effect, blood flow enhancement, change of pH, partial denaturation of tissue and/or any part of the tissue, contraction of the tissue, muscle contraction, relaxation of the tissue, dilatation of the tissue, rejuvenation of the tissue, pain relief, restoration of the connective tissue, altering the shape and/or volume of the tissue, influence on protein synthesis, influence on activity of at least one enzyme, influence on cell metabolism, neocollagenesis, neoelastinogenesis and/or synthesis of any other part of connective tissue, stimulation of hormones, resurfacing of the tissue and/or any other result of applied energy on biological tissue. Disclosed types of biological effect may be combined.

The term "tissue" means in particular but not exclusively pelvic floor tissue including genital tissue, internal tissue of and/or external tissue surrounding the vagina, uterus, vulva, labia minora, labia majora, lamina propria, adjacent muscles, clitoris, cervix, perineum, penis, scrotum, anal canal, rectum. In addition the term "tissue" means mouth, earlobes and/or nose. It may also mean any layer and/or volume of tissue, such as epithelial surface, dermis, adipose tissue, muscularis, mucosal tissue, submucosal layer and gingiva.

The term "treated tissue" means at least part of the surface and/or volume of the tissue influenced by the treatment.

The term "energy delivery element" means an element providing energy to the patient. Also, the term "energy delivery element" should be understood as an energy providing element which may include additional parts; for example, the ultrasound transducer together with the backing material, coupling liquid and acoustic window.

DETAILED DESCRIPTION

Figure 1A:
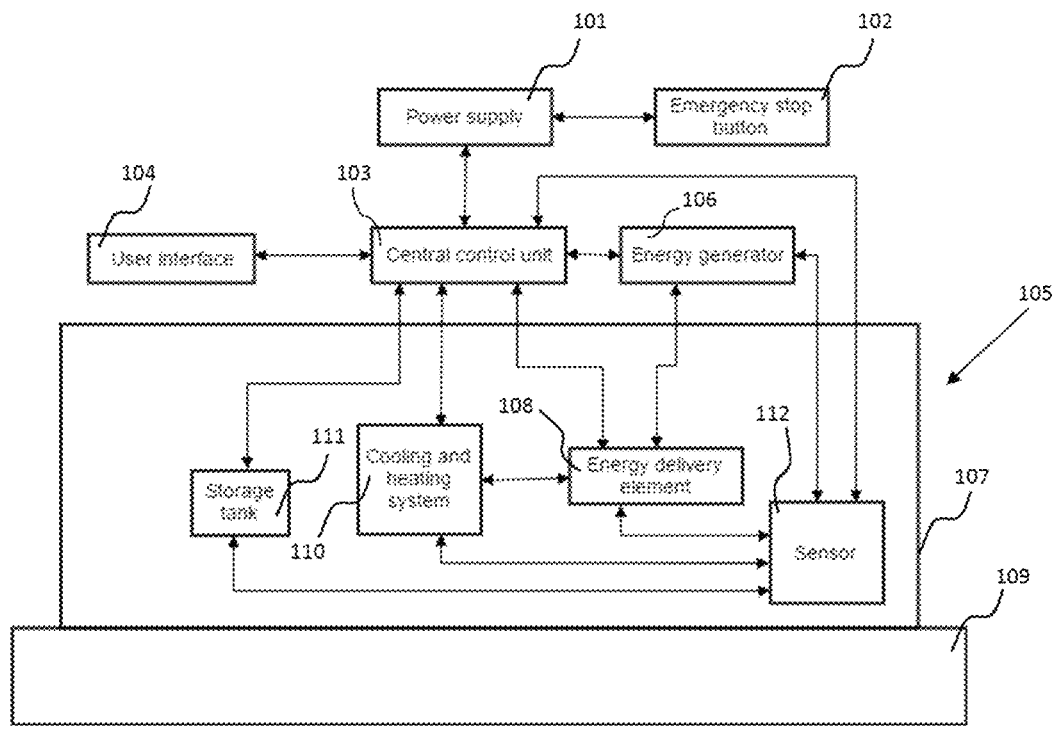
FIG. 1A is schematic diagram of a device for treatment of tissue.

Genital tissue may be divided to female genital tissue and male genital tissue. The external male genital tissue contains the penis and scrotum, internal male genital tissue contains the epididymis, vas deferens and accessory glands. The penis includes erectile tissue. The female genital tissue contains the vulva and vagina. The vulva is an external visible part of the female genital tissue including the mons pubis, labia majora, labia minora, hymen, clitoris, vulvar vestibule, vaginal opening and urethral orifice. Parts of the vulva contain the epithelium, connective tissue and muscularis. The labia majora and mons pubis also contain adipose tissue. The vulva is separated from the anal canal by the perineum.

The human vagina is a canal composed of four layers. The outermost is the epithelium including a nonkeratinized squamous layer. The vaginal epithelium is formed of stratified cells containing a high content of glycogen.

The epithelium may also include bacteria. After desquamation of the stratified cells, the glycogen may be released from the cells and metabolized by lactic bacteria to lactic acid, reducing the pH of the vaginal environment to pH between 4 and 5. Low pH may protect the vagina from colonization by other possibly dangerous bacteria and therefore protect vagina from the inflammation. Some species of bacteria, for example *Lactobacillus, Leptotrichia* and/or *Megashera*, may further improve vaginal health by producing and releasing bacteriocins and other antimicrobial compounds. Colonization of vaginal epithelium by particular bacteria species may be associated with reduced tendency of acquisition and/or transmission of sexually transmitted pathogens. In addition, the presence of particular bacteria may be associated with lower risk of pregnancy-related complications, including pre-term labor. In general, the state of vaginal tissue may help to maintain stability of vaginal environment and health.

A second subepithelial layer, called lamina propria, is a dense tissue layer including fibrillary proteins, collagen, elastin, blood vessels and/or lymphatic vessels. Transudate from these vessels, together with cervical mucus, provides lubrication before and/or during sexual intercourse. Lamina propria includes fibroblasts synthetizing the fibrilllar proteins, e.g. collagen and/or elastin. In addition, the fibrillary proteins may be synthetized by smooth muscle cells. Collagen provides vaginal tissue firmness, while the elastin provides extensibility and elastic recoil. The collagen molecules are formed by a triple-helix fibre structure. Elastin forms an elastic matrix and elastic fibres. Elastin biosynthesis is unique among connective tissue proteins by its limitation to a brief period of development, when elastic fibres produced in the third trimester of foetal life last the rest of life. This limitation, related to most organs and undisturbed tissues, is not present in the female genital tissue, where elastic fibre turnover is continuous.

The third layer, the muscularis, includes smooth muscles. Muscularis and lamina propria, provide a tensile firmness to the vaginal wall. Muscles are in complex interaction with connective tissue of the urethra and vaginal wall.

The fourth layer, the adventitia, is a connective tissue layer separating the muscularis of the vagina and paravaginal tissue. The adventitia contains elastin, collagen and fibroblasts, which may synthetize them. The adventitial fibroblasts may produce fibronectin. Fibronectin is essential for the conversion of fibroblasts to activated myofibroblasts involved in complex cellular functions including tissue repair.

Connective tissue contains at least one protein e.g. collagen; elastin; fibronectin; laminins; glycoproteins; proteoglycans and/or matricellular proteins.

Collagen includes twenty-eight different collagen types which are synthesized by cells, mainly by fibroblasts and/or by muscles. Fibrillar collagen (types I, II, III, V, XI, XXIV and XVII) provide strength, while other types may interact with basal membrane and/or with the fibrillary collagen in order to link the fibrils together or with other molecules of extracellular matrix. Elastin is a stable protein and provides elasticity.

Proteoglycans and glycoproteins interact with growth factors, cytokines and chemokines, cell surface receptors and other molecules of extracellular matrix. They participate in cell procedures such as signaling, proliferation, migration, differentiation, apoptosis and adhesion.

Fibronectin is another fibrillar protein synthesized primarily by fibroblasts. Laminins are glycoproteins influencing cell migration, adhesion and differentiation. They also contribute to blood vessel growth and maturation.

Matricellular proteins play role in organization of extracellular matrix, namely in collagen fibrils, elastin and fibronectin arrangement. They also have significant role in the interactions of the molecules of the extracellular matrix.

Methods and devices are described for prevention and/or treatment of vaginal laxity, vulvar laxity, vaginal dryness by improving humidity, stabilization of vaginal environment, vulvar atrophy, vaginal atrophy, stress urinary incontinence, dysmenorrhea, dyspareunia, muscle spasms, anorectal abscess, anal fistula, rectal pain, haemorrhoids and or anal laxity. These methods and devices may also be used for sexual enhancement, erectile issues, increase of local circulation (e.g. blood or lymph). Other treatments may include prevention and/or treatment of cervicitis, vaginitis, abscess of vulva, bartholinitis, cervical dysplasia, vulvar dysplasia, vaginal dysplasia, leukoplakia of cervix, leukoplakia of vagina, tight vaginal opening, genital warts, candiasis, lichen planus, vulval dermatitis, prostatic hyperplasia and/or vulvar hypertrophy, vaginal bleaching and anal bleaching. The present methods and devices may also be used for labia majora alteration, labia minora alteration and/or clitoral hood reduction.

Treatment of vaginal, vulvar and anal laxity by tightening the tissue may provide increased sexual pleasure. Treatment of erectile tissue located in mons venus, penis, vulvar vestibule, labia minora and/or clitoris may induce angiogenesis, repair of the tissue, synthesis of the tissue and/or enhancement of local circulation.

The present methods and devices may induce a biological effect. The energy transfer may cause at least partial denaturation of connective tissue (e.g. collagen, elastin, fibronectin). It may lead to rejuvenation and/or deposition of at least part of connective tissue by fibroblasts and/or smooth muscle cells or lead to proliferation of at least one fibroblast to myofibroblast.

The method may include application of energy to at least one tissue layer and/or a volume of the tissue, such as the pelvic floor, genital tissue, tissues of perineal region and/or canals. Treatment may be contact, indirect contact and/or with no contact provided by the device positioned adjacent to the tissue of the patient. Energy may be applied in a continuous and/or pulsed manner. Energy may be delivered by one or more energy delivery elements.

The energy transfer may be used for improvement of activity of at least one enzyme e.g. at least one of lysyl oxidase, matrix metalloproteases and/or drug-metabolizing enzymes. Vaginal environment stability may be maintained by application of energy to the tissue to enhance proliferation and/or desquamation of at least one layer. Desquamated tissue containing glycogen may be utilized as a nutrient supply by bacteria, including *Lactobacillus* species, *Leptotrichia* and/or *Megashera*.

The application of electromagnetic energy may lead to heating of the tissue. Energy flux provided by radiofrequency energy may be in the range of 0.001 W·cm-2 to 1500

W·cm-2, more preferably in the range of 0.01 W·cm-2 to 1000 W·cm-2, most preferably in the range of 0.5 W·cm-2 to 500 W·cm-2.

The heating may induce the relaxation of the heated tissue, blood flow enhancement, relief of pain and/or at least partial denaturation of the connective tissue and/or its parts. Heating may also induce analgesic effects and/or myorelaxation.

In one embodiment the radiofrequency energy may be in the range of 10 kHz to 300 GHz, more preferably in the range of 300 kHz to 10 GHz, most preferably in the range of 400 kHz to 6 GHz. In another embodiment, the radiofrequency energy may be in the range of 100 kHz to 550 MHz, more preferably in the range of 250 kHz to 500 MHz, even more preferably in the range of 350 kHz to 100 MHz, most preferably in the range of 500 kHz to 80 MHz. Additionally, the radiofrequency energy may be in the range of 100 kHz to 50 MHz, more preferably in the range of 250 kHz to 10 MHz. Output may be up to 450, 300, 250 or 200 W. The method and device may include operation of the device in the ISM bands of 6.78 MHz, 13.56 MHz, 27.12 MHz, 40.68 MHz, 433.92 MHz, 915 MHz, 2.45 GHz and 5.8 GHz.

Applied energy may include light which may provide heating, myorelaxation effect and/or biostimulation. Light in the range of 620 to 750 nm may be beneficial for local circulation enhancement, restoration of connective tissue, light in the range of 400 to 500 nm may provide bactericidal effect, light in the range of 560 to 60 nm may stimulate tissue rejuvenation. All these types of light may be applied.

Light may be monochromatic or polychromatic. Light may be applied in pulses with duration in the range of 0.1 μs to 10000 ms, more preferably in the range of 1 μs to 5000 ms, even more preferably in the range of 2 μs to 2500 ms, most preferably in the range of 5 μs to 1000 ms. The wavelength of the light may be in the range of 200 nm to 15000 nm, more preferably in the range of 250 nm to 10000 nm, even more preferably in the range of 300 nm to 5000 nm, most preferably in the range of 400 nm to 3000 nm. Energy flux provided by light may be in the range of 0.005 W·cm-2 to 75 W·cm-2, more preferably in the range of 0.01 W·cm-2 to 60 W·cm-2 and most preferably in the range of 0.01 W·cm-2 to 50 W·cm-2. Method and device may also include spot size defined as surface of tissue treated by the light. Spot size may be in the range of 0.01 cm2 to 600 cm2, more preferably in the range of 0.05 cm2 to 550 cm2, most preferably in the range of 0.1 cm2 to 520 cm2.

Energy may be also applied in the narrower spectral band. Some of the spectral bands may represent different colors of the visible part of the electromagnetic spectrum. The wavelength of the applied light may be close to 254 nm, 405 nm, 450 nm, 530 nm, 560 nm, 575 nm, 640 nm, 685 nm, 830 nm and/or 1064 nm. Term "close to" refers to deviation of 20%, more preferably 15%, most preferably 10% from the nominal wavelength.

According to one embodiment, the low level light may be used. The output of the source may be in the range of 0.1 mW to 600 mW, more preferably in the range of 1 mW to 500 mW, even more preferably in the range of 1.5 mW to 475 mW, most preferably in the range of 3 mW to 450 mW. Energy flux provided by low level light may be in the range of 0.01 W·cm-2 to 30 W·cm-2, more preferably in the range of 0.05 W·cm-2 25 W·cm-2 and most preferably in the range of 0.1 W·cm-2 20 W·cm-2.

According to another embodiment, high level light may be used. In this case, the output of the source may be in the range of 0.1 W to 30 W, more preferably in the range of 0.2 W to 25 W, most preferably in the range of 0.35 W to 15 W. Energy flux provided by high level light may be in the range of 0.01 W·cm-2 to 50 W·cm-2, more preferably in the range of 0.05 W·cm-2 to 40 W·cm-2 and most preferably in the range of 0.1 W·cm-2 to 35 W·cm-2.

Applied energy may include mechanical energy. Mechanical energy may provide focused and/or unfocused heating, cavitation, microbubbles formation, muscle stimulation, stimulation of healing process, blood flow stimulation and/or stimulation of inflammatory response.

Optionally, the application of the mechanical energy may lead to creation of focus in desired depth of the tissue and/or defocusing the energy into larger area of the tissue. Treatment depth of the mechanical energy may be in the range of 0.1 to 100 mm, more preferably in range of 0.2 mm to 50 mm, most preferably in range of 0.25 mm to 25 mm, most preferably in the range of 0.3 to 15 mm under the surface of treated tissue. Treatment depth may be influenced by focusation, defocusation and/or frequency of mechanical energy.

The frequency of the ultrasound energy may be in the range of 20 kHz to 25 GHz, more preferably in the range of 20 kHz to 1 GHz, even more preferably in the range from 50 kHz to 250 MHz, most preferably in the range of 100 kHz to 100 MHz. Energy flux provided ultrasound energy may be in the range of 0.001 W·cm-2 to 500 W·cm-2, more preferably in the range of 0.005 W·cm-2 to 350 W·cm-2, most preferably in the range of 0.05 W·cm-2 to 250 W·cm-2.

Mechanical energy may be shock wave energy, where shock waves may provide pain relief, blood flow enhancement, myorelaxation and mechanical stimulation.

Shock waves are characterized by steep pressure amplitude growth in comparison to the surrounding pressure and their non-linear wave propagation. Also, shock waves are characterized by swift positive pressure increase with positive peak pressure amplitudes in the range of 0.1 MPa to 150 MPa or 3 MPa to 150 MPa or 7 MPa to 150 MPa. Shock wave energy may be generated by electrohydraulic, piezoelectric, electromagnetic, pneumatic and/or ballistic principle. The repetition rate of shock wave energy may be in the range of 0.1 Hz to 1000 Hz, more preferably in the range of 0.1 Hz to 750 Hz, even more preferably in the range of 0.5 Hz to 600 Hz most preferably in the range of 1 Hz to 500 Hz. Energy flux provided by shock wave energy may be in the range between 0.0001 W·cm-2 and 50 W·cm-2, more preferably in the range between 0.0001 W·cm-2 and 35 W·cm-2, most preferably in the range between 0.0001 W·cm-2 and 25 W·cm-2.

In one embodiment ballistic shock waves may be used. Ballistic shock waves may be generated by striking of a bullet inside a guiding tube to a percussion guide. The bullet may be accelerated by pressurized gas, spring, electric field, magnetic field or other technique. The repetition rate of the ballistic shock wave may be in the range of 0.1 Hz to 150 Hz or 0.5 Hz to 100 Hz or 1 Hz to 60 Hz.

Applied energy may be electric energy which may provide muscle stimulation, analgesic effect, contraction of muscles and/or myorelaxation effect.

Electric energy may be applied in a constant current mode. In this case, the output current may be in the range of 0.01 mA to 400 mA or 0.01 mA to 300 mA, or 0.01 mA to 180 mA. Output voltage may be in the range of 0.001 V to 350 V or 0.001 V to 300 V or 0.001 V to 250 V.

Electric energy may be applied in a constant voltage mode. In this case, the output current may be in the range of 0.01 mA to 400 mA or 0.01 mA to 300 mA or 0.01 mA to 180 mA. Output voltage may be in the range of 0.001 V to 350 V or 0.001 V to 300 V or 0.001 V to 250 V.

Electric energy may provide the high voltage therapy. In this case, the output current may be in the range of 0.01 mA to 50 mA or 0.01 mA to 30 mA or 0.01 mA to 15 mA. Output voltage may be in the range of 0.001 V to 800 V or 0.001 V to 650 V or 0.001 V to 600 V.

In a microcurrent application, the output current may be in the range of 0.001 mA to 10 mA or 0.001 mA to 5 mA or 0.001 mA to 3 mA. Output voltage may be in the range of 0.001 V to 250 V or 0.001 V to 200 V or 0.001 V to 150 V.

Electric energy may be applied in pulses. The repetition rate of pulses may be in the range of 0.001 Hz to 1000 Hz or 0.05 Hz to 800 Hz or 0.1 to 600 Hz. The repetition rate of pulses may induce various effects. The repetition rate of pulses inducing muscle stimulation may be in the range of 0.01 Hz up to 100 Hz or 0.05 Hz to 85 Hz or 0.1 Hz to 75 Hz. The repetition rate of pulses inducing pain relief may be in the range of 100 Hz up to 400 Hz or 105 Hz to 250 Hz or 115 Hz to 150 Hz. The repetition rate of pulses inducing a myorelaxation may be in the range of 100 Hz up to 600 Hz or 130 Hz to 400 Hz or 150 Hz to 250 Hz. Amplitude of applied current may vary following the patient needs and/or desired effect.

Applied energy may be magnetic energy which may provide at least partial muscle contraction, myorelaxation effect, stimulation of one or more muscle fibre and/or analgesic effect. A device and method for generation of magnetic energy is described in co-pending applications PCT/IB2016/053930, U.S. 62/357,679, U.S. Ser. No. 15/396,073, U.S. Ser. No. 15/404,384, U.S. Ser. No. 15/344,811, U.S. Ser. No. 15/073,318 which are incorporated herein by reference. Magnetic flux density of the magnetic energy may be at least 0.1, 0.5, 1, 2 T or up to 7 T at repetition rate at least 0.1, 1, 10, 30, 50, 55, 60 or up to 700 Hz with treatment/successive treatments lasting several seconds or longer, for example, for at least 5, 10, 30, 60, 120 or 240 seconds or longer. The impulse duration may be in the range of tens to hundreds of µs. The magnetic energy may by static and/or time variable (e.g. monophasic or biphasic).

The magnetic energy may be modulated. In one embodiment the magnetic flux density is varied, while the repetition rate of the time varying magnetic energy is the same as impulse duration. In another embodiment the repetition rate may be varied while the impulse duration and magnetic flux density is constant. In still another embodiment the impulse duration may be varied while the repetition rate and magnetic flux density may remain constant.

Applied energy may be plasma such as nonthermal plasma (called also cold plasma) may be used. Application of plasma may be used for reduction and/or elimination the possible discomfort of the patient (e.g. bleeding, pain) before, during and/or after the treatment. Application of nonthermal plasma may stimulate regenerative processes by wound healing enhancement and or blood coagulation. Nonthermal plasma may be bactericide and therefore may decrease the risk of the inflammation.

Plasma may be also supplemented by another substance e.g. gas, radical, radical precursor and/or radical scavenger. The other substance may be nitric oxide and its radicals. Temperature of generated plasma may be between 18° C. to 65° C., more preferably between 25° C. to 62° C., even more preferably between 30° C. to 60° C., most preferably between 32° C. to 40° C. Plasma may be applied in range between 1 s to 60 min, preferably between 10 s to 40 min, even more preferably between 30 s to 30 min. Plasma may also be applied in pulses that may last between 0.1 s to 30 s, 20 s, and/or 10 s. The most preferred embodiment produces plasma by voltage between electrodes in range between 100 V to 30 kV in more preferred embodiment between 1 kV to 30 kV in the most preferred embodiment in range between 1 kV to 20 kV. Plasma generation may use an electrode frequency of 20 kHz to 27 MHz in more preferred embodiment between 0.8 MHz to 15 MHz or in the most preferred embodiment between 1 MHz to 14 MHz.

Energy may be a thermal and/or cooling energy represented by an application of the heated and/or cooled fluid to the tissue. Fluid may be applied directly on the tissue.

The application of the first type of energy may also overlap with the application of second type of energy. The overlap of the first type of energy with the second type of energy may occur at discrete time intervals in the range of 0.01 to 100 seconds, more preferably in the range of 0.05 to 80 seconds, most preferably in the range of 0.1 to 60 seconds. The application of electromagnetic energy may be concurrently applied with the mechanical energy e.g. ultrasound energy transferred through the surface of same energy delivery element e.g. capacitive electrode.

The energy transfer may increase the temperature of the tissue in the range of 30° C. to 105° C., more preferably in the range of 32° C. to 70° C., even more preferably in the range of 34° C. to 55° C., even more preferably in the range of 35° C. to 48° C., most preferably in the range of 35° C. to 44.5° C. Optionally, the temperature of the tissue may be increased in the range 40.5° C. to 43.5° C.

The tissue may be cooled by a cooling and heating system. One or more layers and/or volumes of the tissue may be cooled. The one or more layers may be cooled, while the other layers may be heated. Optionally, tissue in one tissue layer may be heated while the non-treated tissue in the same tissue layer may be cooled by the device. Temperature of the tissue may be reduced in the range of −25° C. to 37° C., more preferably in the range of −15° C. to 30° C., even more preferably in the range of −10° C. to 28° C., most preferably in the range of −2° C. to 25° C. The tissue may also be cooled in order to maintain the normal body temperature on the surface while heating the inner layer or layers.

Treatment may include a treatment cycle of heating and cooling. The time interval of a cycle may be in the range of 0.05 to 1200 seconds, more preferably in the range of 0.01 to 1000 seconds, most preferably in the range of 0.5 to 800 seconds. The heating part of the treatment cycle of heating and cooling is preferably in the range of 0.1% to 90% of the cycle, more preferably in the range of 10% to 80% of the cycle, most preferably in the range of 35% to 70% of the cycle.

The method and device may use any type of energy mentioned in the Glossary. In addition, the method and device may use energy combination. The energy combination may be a combination of electromagnetic energy, electric energy, mechanical energy, thermal energy, magnetic energy and plasma with each other. A combination of electromagnetic energy and mechanical energy or plasma may be used. A combination of electromagnetic energy and magnetic energy or electric energy may be used. In another embodiment a combination of electromagnetic energy and thermal energy may be used, wherein the applied fluid may be heated by electromagnetic energy. Optionally, more types of electromagnetic energy may be used. Light may be combined with radiofrequency energy or microwave energy or radiofrequency energy may be combined with microwave energy. Optionally, types of mechanical energy, namely shock waves and ultrasound may also be combined.

Application of energy combinations may lead to higher comfort of the patient. By combining of first energy and second energy, the total output needed to provide a therapeutic effect may be the sum of the output of first and second type of energy. Therefore the output of one type of energy may be lower, because the combination with at least one other type of energy may provide sufficient therapeutic effect. Decreased output of one type of energy may reduce the possibility of burning, itching and/or pain.

Output of the first energy may participate in the total output pf the energy combination by portion of at least 50%, more preferably by portion of at least 55%, most preferably by portion of at least 65%.

One or more applicators being parts of device may be used. The applicator may be positioned adjacent to the tissue and transfer energy into the tissue causing a biological effect. The applicator may include one or more detachable parts wherein the detachable part may be exchanged by the user in order to vary the treatment. The applicator may have one or more detachable part.

The physical appearance of the applicator (e.g. shape, size, length, width and/or elasticity) may be changed by adding and/or exchanging one or more detachable parts. Different and exchangeable detachable parts may provide operator choices of any physical appearance in order to sufficiently treat the tissue. The applicator may be assembled with a chosen length. Different parts of the applicator may have various widths to conform to anatomy of the body canals (e.g. vagina). Optionally, the utilization of one or more detachable parts may provide the applicator with none, one or more energy delivery elements located based on the operator's need. Such methods and devices may provide the applicator with adaptive detachable parts resolving problems of ineffective and uncomfortable treatment.

Detachable parts may include one or more energy delivery element for delivering energy to tissue. Optionally the detachable parts may not include any energy delivery element and be used e.g. for elongation of the applicator. Detachable parts may have various shapes, e.g. spherical, hemispherical, pyramidal, cuboid, prismatic, conical, annular and cylindrical. Prisms may have the base created by at least three, four or five lines creating triangular, tetragonal or pentagonal prism.

One or more detachable parts may be joined to one or more attaching elements which may contain a handle. A detachable part may be joined to another detachable part or attaching element containing the handle by e.g. a revolving mechanism.

One detachable part may be exchanged for another detachable part. In one exemplary embodiment a detachable part containing one energy delivery element may be replaced by different detachable part containing another one or more energy delivery element providing the same type or a different type of energy. A detachable part containing single energy delivery element may be replaced by different detachable part containing at least two energy delivery elements. In still another embodiment a detachable part containing single delivery element may be replaced by different detachable parts containing at least one or two energy delivery elements, where at least one energy delivery element located of the first detachable part may deliver same type of energy as the energy delivery element located of the second detachable part.

An applicator and/or one or more of its detachable parts may provide a sum of energy flux of the first energy and the second energy in the range between 0.0001 W·cm-2 to 2500 W·cm-2, more preferably in the range between 0.005 W·cm-2 to 1500 W·cm-2, most preferably in the range between 0.05 W·cm-2 to 1000 W·cm-2.

Any type of substance may be used before, after and/or during treatment. The substance may change the characteristics of the tissue e.g. provide analgesic effect, absorb applied energy, cause another biological effect to the treated tissue and/or target non-treated tissue in order to prevent the unintended biological effect in the treated tissue.

Optionally a fluid may be applied on the device and/or tissue to provide comfortable treatment and/or sufficient contact of the device and tissue. The fluid may be a hydrophobic or hydrophilic material having properties of a gel. Fluid may be applied from a reservoir.

The device of FIG. 1A may contain a power supply 101, which may include an emergency stop button 102. The emergency stop button 102 may be located in the patient controller. Power supply 101 may be connected to the central control unit 103, which may control one or more applicators 105. Central control unit 103 may be printed circuit board which may include processor. Central control unit 103 may contain and/or be connected to user interface 104. Connection of the central control unit 103 to the user interface 104 may be by wire and/or wireless. Power supply 101 may be part of the applicator 105 in the form of a disposable or rechargeable battery or power plug or standard power cord. Central control unit 103 may be also positioned in the applicator 105 or outside the applicator 105. Central control unit 103 may provide additional treatment control such as stabilization of the treatment parameters, for example frequency, power, impedance or temperature of treated tissue. Additional treatment control may be independent on the operator and may be provided because of safety of the treatment. Central control unit 103 may be coupled and/or communicate with storage tank 111, cooling and heating system 110, energy delivery element 108, power supply 101, energy generator 106 and/or sensor 112.

User interface 104 may be e.g. notebook, PC, mobile phone, tablet and/or control panel including a display, buttons and/or other control members. User interface 104 may contain one or more movement control devices for controlling the movement of the applicator. Such movement control device may include for example a joystick, keyboard, mouse, sleeve and/or electronic glove with the moves virtually transferred to the movement of the applicator and/or device. The applicator may be moved by robotic apparatus controlled by the operator. A movement control panel may be used to move the applicator without the need for the operator to contact intimate parts of the patient. This may reduce discomfort of the patients. A display may be part of the user interface 104 providing set-up of the treatment, providing results of imaging and/or sensing the conditions and/or changes of the conditions of the tissue. Optionally, the display may also visualize the information about the treatment, such as length of the treatment, amount of transferred energy, data from sensors etc. Optionally, the user interface 104 may be part of the applicator 105.

The device may contain an energy generator 106 positioned inside or outside of the applicator 105. The energy generator 106 may generate and/or regulate one or more types of energy for treatment. The device may include more than one energy generator 106 (e.g. in case of more than one type of energy delivered to the body). The energy generator 106 may, if used may include a high frequency (HF) generator and transmatch adjusting the input impedance to the impedance of the treated tissue in order to maximize the power transfer. The energy generator 106 may also contain balun transformer.

The device may be in direct contact (shown in FIG. 1A), indirect contact (shown in FIG. 1B) or in no contact with the tissue 109.

In the case of direct contact, shown in FIG. 1A, the device (e.g. casing 107 or energy delivery element 108) may contact the tissue 109. Treated tissue may be tissue layer and/or tissue layers in direct contact and/or may be located below the contacted layer or layers of the tissue.

Figure 1B:
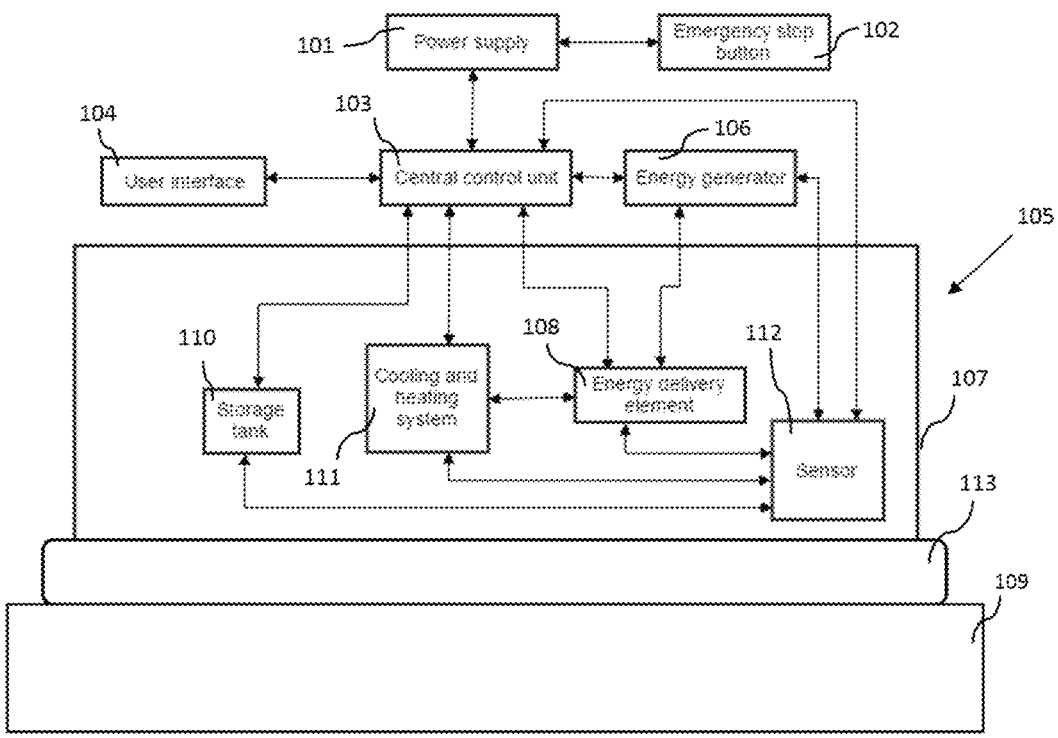
FIG. 1B is another schematic diagram of a device for treatment of tissue.

In case of indirect contact, shown in FIG. 1B, the gap between the tissue and the applicator may be filled by one or more spacing objects 113 (e.g. foam, bolus filled with fluid, waveguide, solid insulator, textile, solid mask and/or solid mask with holes). The spacing object 113 may cover at least part of surface of the applicator 105 and may be moved before, during and after the treatment by an automated system and/or manually. The spacing object may be profiled i.e. be thinner below the center of the energy delivery element than on the edge of the energy delivery element. The thickness of profiled spacing object below the center of the energy delivery element may at least 0.1 mm or 0.5 mm or 1 mm or 2 mm and up to 20 mm. Optionally, the thickness of the spacing object below the edge of energy delivery element may be at least 5% or 10% or 20% or 50% or 100% or 300% thicker than below the center of the energy delivery elements. The spacing object 113 may be detachable from the applicator 105. One or more spacing objects 113 may be positioned on the tissue separately from the applicator 105 prior the treatment. In another configuration, a plurality of spacing objects may be positioned on different parts of the surface of the tissue and the applicator is mounted to every one of them during the treatment. Spacing objects may be disposable or reusable e.g. after sterilization by autoclaving, gamma ray radiation, X-ray radiation and/or chemical sterilization.

In case of no contact with the tissue, the applicator may be spaced from the tissue by a gap filled e.g. by air. Preferred embodiments of this configuration are described below. The direct, indirect and/or method of the treatment with no contact may be changed during the treatment.

The device may contain functional parts e.g. a cooling and heating system 110, storage tank 111, energy delivery element 108 and sensor 112. These functional parts may be connected to the central control unit 103. Optionally, these parts may be located outside the applicator 105.

The device may contain a cooling and/or heating system 110. The cooling may be used for maintaining an increase or decrease in temperature of the device, applicator, energy delivery element and/or tissue. In first embodiment temperature-transferring media may be used. The media may be fluid (e.g. liquid or gas, preferably air) or a solid temperature-transferring part. Fluid may flow near and/or in contact with the energy delivery element 108 or any other part of device. The solid temperature-transferring part may be a thermoelectric device in contact with an electrode and/or the tissue. The flow of fluid may be provided by a blower or suction mechanism. The thermoelectric device may be also used for cooling the flowing fluid, which may then cool the device. In another embodiment the cooling and heating may be provided by a capacitive electrode located inside the device.

The cooling and/or heating system 110 may induce gentle heating. The heating generated by energy delivery element may not provide biological effect. Such change of temperature may be utilized to better match the temperature of the patient's tissue with the device, preventing temperature shock and constriction of the tissue touched by the device, applicator and/or energy delivery element. The cooling and heating system 110 may provide heating used for treatment of the tissue. Such configuration may be used with an energy delivery element 108 providing almost no heating (e.g. magnetic coil). The tissue may be preheated and/or precooled before the start of the therapy.

The spacing object 113 may be also used for providing cooling and/or heating. Temperature-transferring media may be located in the spacing object and/or in the space between the spacing object and the energy delivery element.

The device may contain one or more storage tanks 111 for storing of one or more substances e.g., liquid, gel or gas.

A substance, which may be a liquid, gel and/or gas, may be dispensed on the tissue and/or the part of the applicator. The substance may be dispensed before, during or after treatment. The substance (e.g. hydrating gel or water) may lower friction between the applicator and the tissue or improve conductivity for better energy transfer. In use of another, substance (e.g. antibiotics) may disinfect the surface of the tissue and/or the applicator. A substance (e.g. lidocaine) may provide an analgesic effect. The substance may also be a mixture of pharmaceutical products. The substance may be a single gas or a mixture of gases. Nitric oxide may be used to vasodilation of blood vessels or enhancement of sexual arousal. A gas and/or mixture of gases may be used to create a nonthermal plasma to help with healing of an irritated tissue from application of a capacitive, resistive electrode and/or one or more protruding invasive members (e.g. needles acting as electrodes).

The device may include one or more sensors 112 used for detecting changes or state of the treatment, input energy, transferred energy, reflected energy, tissue, applicator, energy delivery element and/or device.

The sensor 112 may be an acoustic, vibration, chemical, electric, magnetic, radio, flow, navigation, positional, optical, imaging, pressure, force, density, temperature, impedance, current, Hall and/or proximity sensor. The sensor may be also gyroscope, capacitive displacement sensor, thermographic camera, ion selective electrode, pH electrode, and a like.

Measured physical quantities may be energy, output of at least one energy delivery element, impedance, temperature of one or more layers of the tissue, energy delivery element and/or the device, water content of the tissue, phase angle of delivered and/or reflected energy, pH of the environment, density of the tissue and the like.

The imaging sensor may be used for imaging of the region. The imaging sensor may be e.g. one or more cameras, an ultrasound transducer and/or terahertz imaging element. The imaging sensor may be a thermographic camera measuring the temperature of the treated and/or untreated tissue. The temperature sensitivity of the infrared camera may be better than 0.1 K or 0.5 K. The imaging sensor may provide a static picture and/or recorded footage of any abnormality inside the canal and/or cavity, on the visible surface of the tissue and/or in one or more layers of the tissue. The imaging device may be used to control the movement of the applicator by the operator from another room.

One sensor may also measure more than one physical quantity.

The sensor may be also a nerve detector. Such sensor may provide information about a presence of a nerve. For example, the sensor may provide low current to the tissue in order to stimulate the nerves. The response of the tissue may be monitored in order to approximately locate the innervated area.

The sensor may also sense a contact of the applicator with the tissue and/or a distance between the applicator and the tissue. Such sensor may be capacitive and/or impedance sensor. The system and method may be adapted to receive such signal in order to control the contact. Data from such sensor may be used to notify the operator about sufficient and/or unintended contact of the tissue and the device.

Data from one or more sensors may provide feedback of the device. Feedback may include a change of recommended time of treatment, automatic movement of the applicator, change of energy characteristics (e.g. frequency and/or power), change of position of the applicator based on patient's movement and the like. The feedback may include a determination of contact between the applicator and the tissue from the measurement of impedance.

The method and device may include usage of one or more sensors providing guidance to the applicator. A main problem during the treatment is linear movement of the applicator regardless the inner anatomical structure. Improper movement may cause unpleasant or painful treatment and may even lead to damage of the tissue. Use of such sensors may eliminate these treatment problems. The applicator may include one or more sensors, for example a sensor using electromagnetic and/or sound waves. In addition, the applicator and/or device may include a guiding unit (e.g. inertial measurement unit) including at least one or combination of accelerometer, magnetometer and/or gyroscope. A guiding unit may detect movement, velocity, acceleration, vertical position and/or horizontal position of the applicator.

Data from the sensor may provide information about changes related to treatment. If a treatment characteristic exceeds a safety limit, the method and device may generate a signal in human perceptible form, e.g. sound or a color change. More than one signal may be generated. Alternatively, or additionally, and the method and device may immediately or gradually interrupt the treatment. Exceeding a safety limit may be signaled by flashing color LED located in the applicator and/or in the user interface 104 together with a warning sound.

The method and device may include using of one or more applicators 105 containing one or more detachable parts. The device, particularly the applicator, may include one or more energy delivery elements delivering energy to the tissue.

The applicator 105 may be an internal applicator for internal use and/or external applicator for external use. The device may be used with one and/or both applicators. The device may provide treatment of external and internal parts of the tissue using the single applicator resembling a combination of both internal and external applicator. Applicators may be disposable and used for a single treatment or reusable and sterilized after every treatment and reused for another treatment.

The applicator may be made of polymer, metal, textile and/or any other biocompatible material. The materials may be varied, so the whole applicator may be made from variety of the materials. The surface of the applicator may be covered by one or more materials different from the surface material, for example by textile and/or membrane.

The applicator may include at least one focusing element for focusing energy to the point, area and/or layer of the tissue. The focused area may also include one or more layers of the tissue.

The one or more energy delivery elements may be a unipolar, monopolar, bipolar or multipolar electrode; coil; light source (e.g. LED diode, discharge tube, gas-discharge lamp, etc.); mechanical wave transmission element (e.g. piezo element); heating and/or cooling element and/or plasma delivery element. Electrode may be manufactured from aluminum. Energy delivery elements may be activated to deliver energy or deactivated to stop deliver energy.

One or more energy delivery elements may provide energy continuously or discretely e.g. in pulses. Energy delivery elements may be supported by another type of energy. Optionally, one or more energy delivery elements may provide energy discretely, and one or more another energy delivery elements may provide energy continuously.

Energy delivery elements may be provided in various shapes, sizes and orientations. The energy delivery element or elements may create a matrix, where the one or more energy delivery elements may have various shapes e.g. rectangular, circular, oval, annular or helical on the surface and/or encircling around the applicator. Also, one or more energy delivery elements may cover the surface of the detachable part in the range of 0.5% to 100%, more preferably 2% to 100%, even more preferably in the range of 5% to 100%, most preferably in the range of 12% to 100% of the surface of the detachable part.

Figure 2:
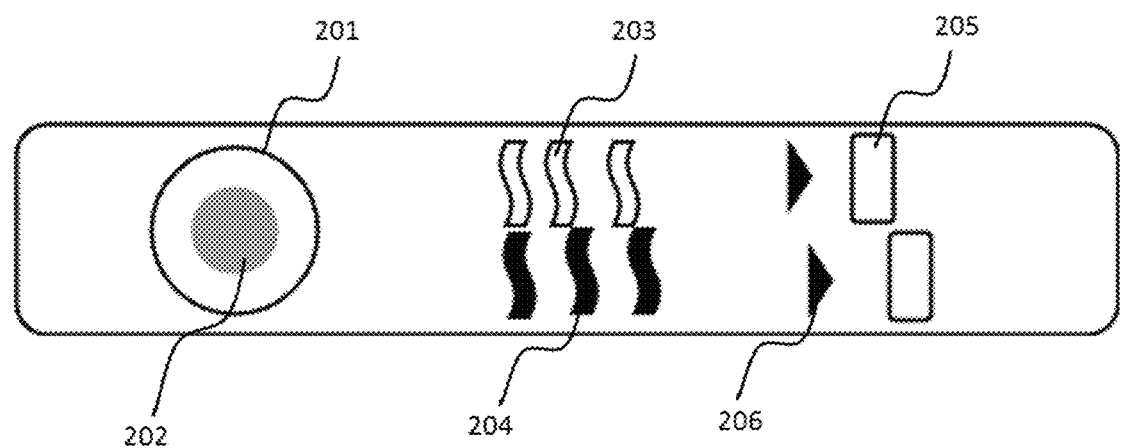
FIG. 2 is an exemplary embodiment of the energy delivery elements located of the applicator.

FIG. 2 illustrates energy delivery elements located on the applicator 105. A first energy element is depicted by a circle 201, while second energy delivery element is shown as a disc 202. In another embodiment energy delivery elements shown as the strips are located near to each other. Strips 203 and 204 may be energy delivery elements of the same or different type of the energy. In another embodiment embedded triangular elements 205 may be energy delivery elements delivering a first type of energy while and the healing delivery element 206 (e.g. plasma delivery element) may be located in a spatially different arrangement.

One or more energy delivery elements may be movable. The movement of one or more energy delivery elements may be circular, linear or in vertical direction in the relation to the treated tissue. These types of movements may be combined. Movement of one or more energy delivery elements may be used for providing a mechanical massage. The position of the one or more energy delivery elements may be adjusted according patient's needs and/or movement.

Treatment by one or more energy delivery elements may be controlled by central control unit 103. The central control unit 103 may provide treatment by one or more energy delivery elements. The central control unit 103 may provide treatment by all energy delivery elements.

One or more energy delivery elements and/or at least part of the energy delivery element may be detachable. An insulating layer of a capacitive electrode may be detachable to change the energy delivery element from a capacitive electrode to a resistive electrode.

The energy delivery element may invasively penetrate into the tissue via a penetrating member such as a needle.

An internal applicator may be positioned into and treat body canals and cavities e.g. the vagina, vulvar vestibule, cervix, urethra, rectum, anal canal, rectum, bladder, nose or mouth. An internal applicator may be also employed to treat external tissue. The labia minora, vulvar vestibule including labia minora and vaginal opening may be treated by an internal applicator.

The internal applicator 301 may be of suitable shape e.g. a tubular and circular shape. The shape may include one or more ridges and/or incurvations providing a broader and/or thinner part.

Figure 3A:
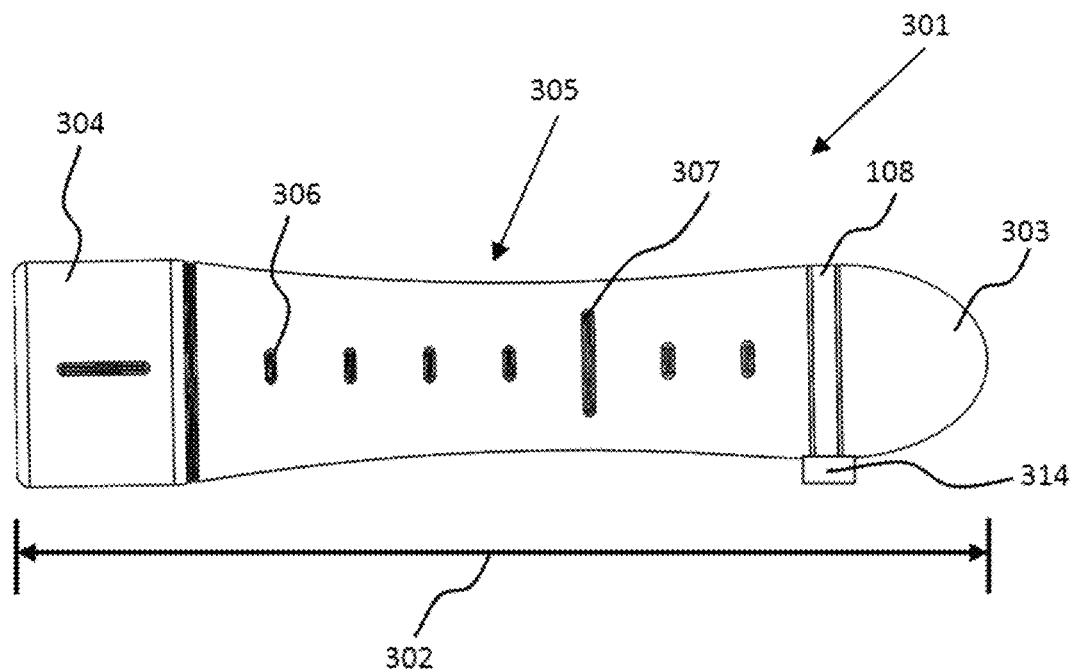
FIG. 3A is a view of an exemplary internal applicator.

FIG. 3A shows one embodiment of an internal applicator 301. The internal applicator 301 may have phallic shape. The length 302 of internally insertable part may be in the range of 0.5 cm to 25 cm, more preferably in the range of 0.75 cm to 20 cm, even more preferably in the range of 1 cm to 18 cm, most preferably in the range of 1.2 to 15 cm. The energy delivery element 108 (e.g. a monopolar capacitive or resistive electrode) is shown as a ring-shaped circular electrode around or encircling the distal part 303 of the applicator, although it may be also semicircular. It may be part of the distal part 303, curvature 305 and/or proximal part 304 of the internal applicator. The energy delivery element may have width and/or length in the range of 0.1 mm to 100 mm, more preferably in the range of 0.3 mm to 80 mm, even more preferably in the range of 0.5 mm to 60 mm, most preferably in the range of 1 mm to 50 mm. The radius of the ring-shaped circular and/or semicircular energy delivery element 108 may be in the range of 0.1 cm to 25 cm, more preferably in the range of 0.2 cm to 20 cm, even more preferably in the range of 0.4 cm to 15 cm, most preferably in the range of 0.5 cm to 12 cm.

The phallic shape of the internal applicator may be altered by the presence of one or more curvatures 305 having a radius of curvature in the range of 50 mm to 600 mm, more preferably in the range of 100 mm to 550 mm, even more preferably in the range of 120 mm to 500 mm, most preferably in the range of 135 mm to 450 mm.

A plurality of marks (e.g. smaller marks 306 and/or larger marks 307). may be equidistant to each other. Distance between the marks may be 0.1 cm or 0.2 cm or 0.25 cm or 0.5 cm or 1 cm or 1.5 cm and/or 2 cm. The marks may determine the length and/or volume of the applicator inserted into the body cavity and/or canal.

The internal applicator may include at least one temperature sensor 320, e.g. thermocouple, thermistor and a like. Temperature sensor 320 may be embedded inside the wall of the applicator or may be attached to the applicator. The temperature sensor 320 may be in contact with the tissue. The temperature sensor 320 may detect temperature of the energy delivery element and/or temperature of the tissue e.g. epithelium and/or lamina propria. Also the temperature sensor 320 may detect temperature of the volume of the tissue in direct contact with energy delivery element and/or volume of the tissue which is not in direct contact with energy delivery element.

Figure 3B:
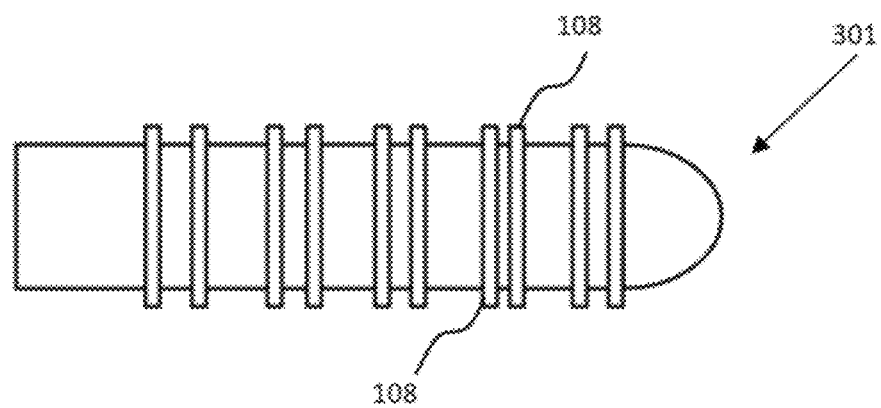
FIG. 3B is another view of an exemplary internal applicator.

FIG. 3B shows another embodiment, where the internal applicator 301 may carry one or more ring-shaped circular and/or semicircular energy delivery elements 108, e.g. bipolar or monopolar electrodes, where complementary pairs of ring-shaped circular electrodes encircling the applicator may be positioned close to each other. Optionally, the energy delivery element may be divided into segments, as shown on the FIGS. 4A-B. Distance between two energy delivery elements may be in the range of 0.01 mm to 20 mm, more preferably in the range of 0.05 mm to 15 mm, even more preferably in the range of 0.2 mm to 12 mm, most preferably in the range of 0.5 mm to 10 mm. Length of ring-shaped energy delivery elements encircling the applicator may be in the range of 0.1 mm to 100 mm, more preferably in the range of 0.3 mm to 80 mm, even more preferably in the range of 0.5 mm to 60 mm, most preferably in the range of 1 mm to 50 mm. The radius of the ring-shaped circular and/or semicircular energy delivery element 108 may be in the range of 0.1 cm to 25 cm, more preferably in the range of 0.2 cm to 20 cm, even more preferably in the range of 0.4 cm to 15 cm, most preferably in the range of 0.5 cm to 12 cm.

The energy delivery elements of the internal applicator may not touch the tissue at all. The one or more energy delivery elements can be located inside the curvature 305, which may be located in the free space formed by wider part of the applicator surrounding the ridge. The internal applicator may include a grid contacting the tissue and spacing the tissue from the energy delivery element.

Figure 3C:
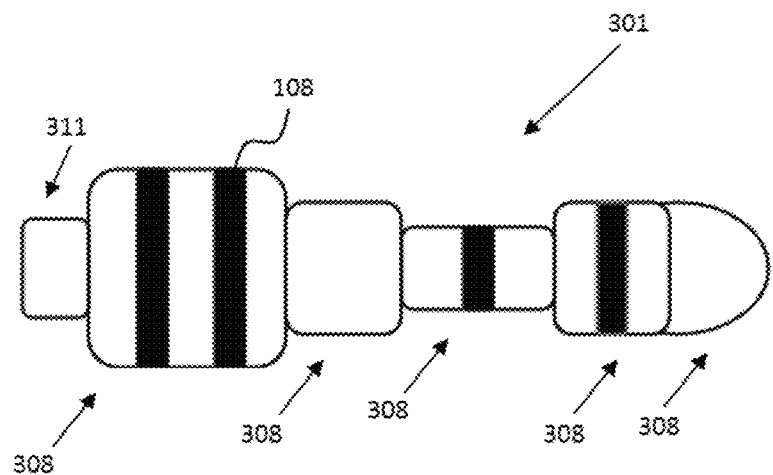
FIG. 3C is another view of an exemplary internal applicator.

FIG. 3C shows an embodiment of the internal applicator divided into several e.g. circular or semicircular detachable parts 308 attached to attaching part 311, some of them carrying their own energy delivery element 108 encircled around them. The detachable parts 308 have various lengths, shapes and/or widths. Therefore, they may be combined to create a differently sized and ridged applicator.

Figure 3D:
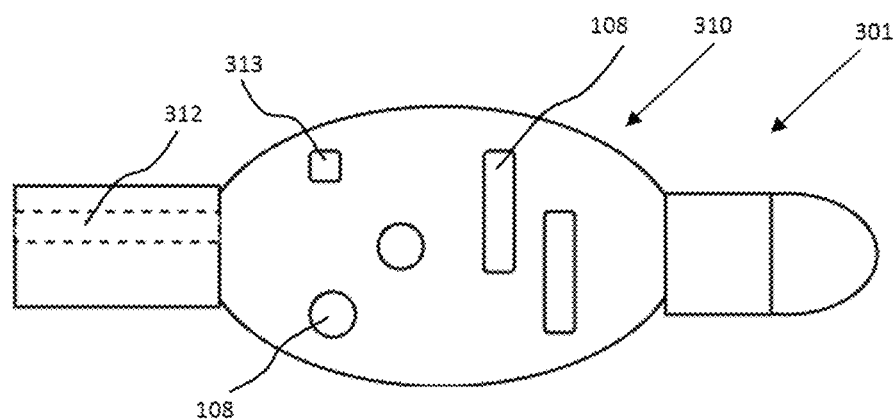
FIG. 3D is another view of an exemplary internal applicator.

In FIG. 3D the internal applicator 301 may include one or more expandable elements 310 made from elastic material, where one or more energy delivery elements 108 is located on the surface of the expandable element 310. FIG. 3D shows more energy delivery elements 108 with different shapes. One or more expandable elements 108 may also be detachable parts. During the treatment, the expandable element 310 may be filled with fluid. Filling fluid may be warm or cold and be stored outside the internal applicator 301 and/or inside the storage tank 111. In both cases, the fluid may be transferred to expandable element 310 by one or more nozzle 312. Then, the fluid may be drained from the expandable element 310 by the same nozzles.

The cold fluid may cool the tissue during application of the energy while the warm fluid may provide relaxation to the tissue and ensure the deeper insertion of the applicator. Presence of cold fluid and warm fluid may be alternated in time periods. By alternating cold-warm fluid, the first fluid may be present in the range of 5% to 100%, more preferably in the range of 10% to 100%, even more preferably in the range of 20% to 100% of total therapy time. The expandable element may be partially or totally filled at specific times during the treatment. Partial filling may be used for prevention of shock or injury of the tissue. The volumetric flow rate through one nozzle during the transfer of the fluid in and/or out the expandable element may be in the range of 0.001 mm3/s to 1 dm3/s, more preferably in the range of 0.1 mm3/s to 0.5 dm3/s, even more preferably in the range of 0.15 mm3/s to 0.25 dm3/s, most preferably in the range of 0.2 mm3/s to 0.1 dm3/s. The expandable element 310 may include a pressure sensor and/or a proximity sensor 313. A proximity sensor may be positioned on the surface of and/or in the expandable structure. The proximity sensor may be impedance sensor.

Figure 3E:
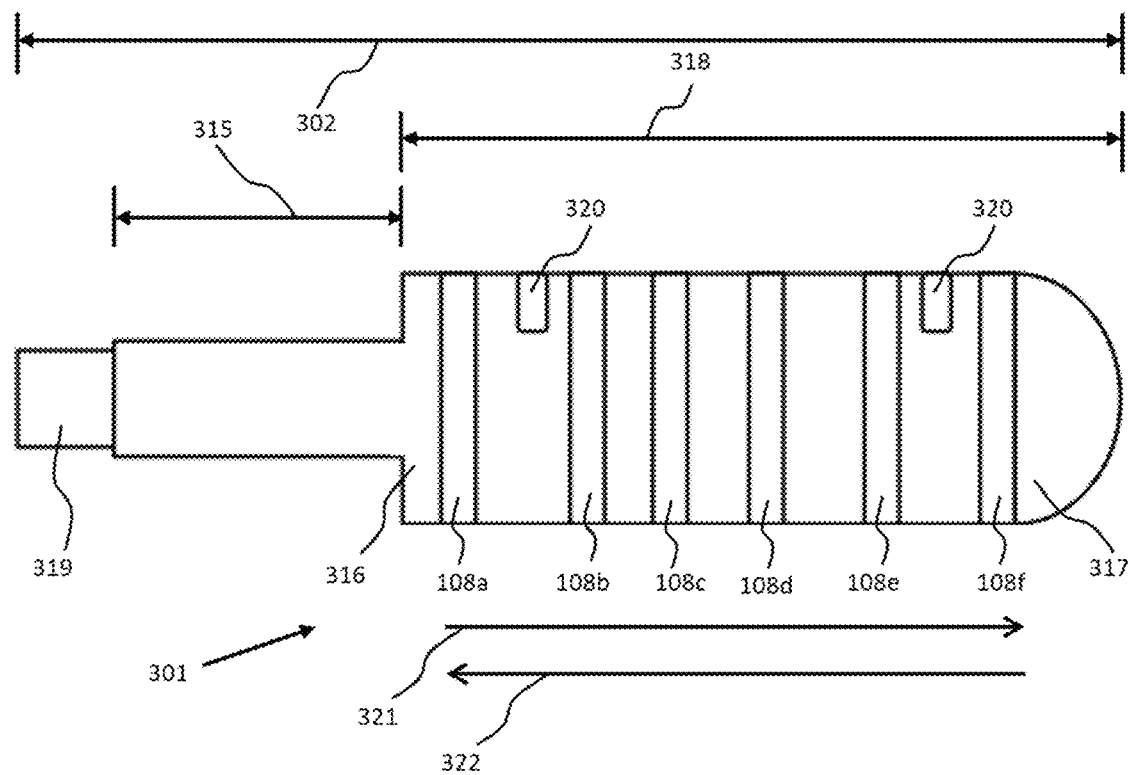
FIG. 3E is another view of an exemplary internal applicator.

FIG. 3E shows embodiment of internal applicator 301 similar to 3B having an insertable part 318, which may be inserted into body canal or cavity (e.g. vagina or anal canal) and non-insertable part 315 (may be omitted). The internal applicator 301, insertable part 318 and/or non-insertable part 315 may be a detachable part. The insertable part 318 may include a proximal part 316 and a distal part 317 including plurality of energy delivery elements 108*a-f*. The insertable part 318 may be positioned to the body canal or cavity on the beginning of the treatment, which may then proceed without additional movement of the insertable part 318. Internal applicator 301 may be coupled to attaching part 311 through at least one wire and/or connector.

Figure 3F:
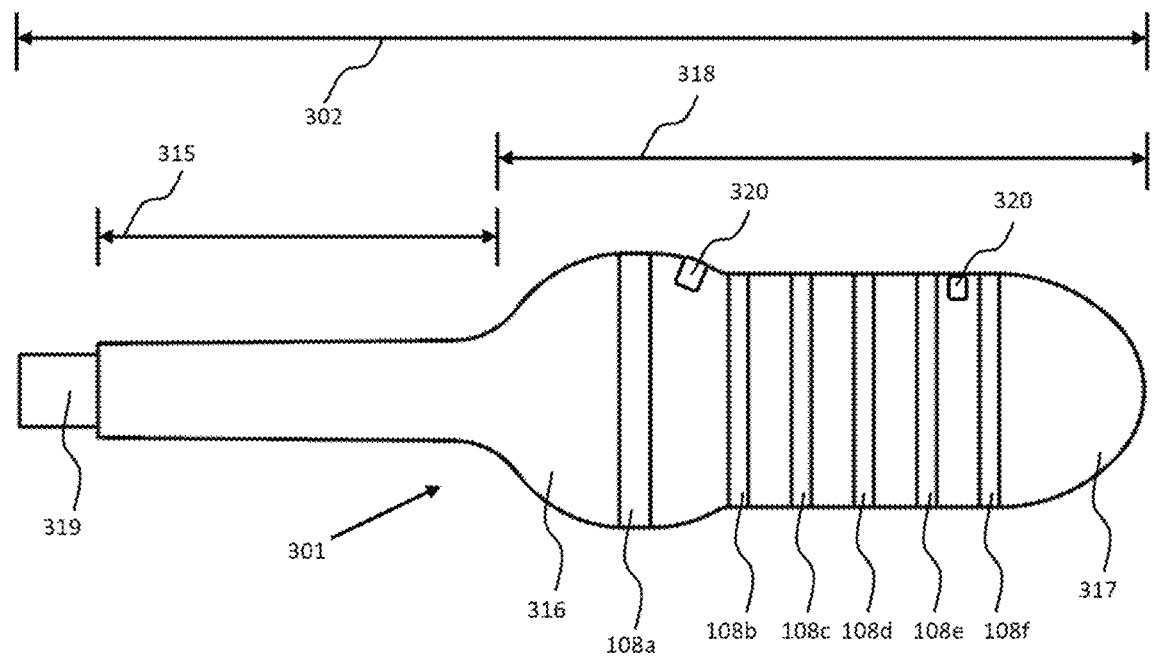
FIG. 3F is another view of an exemplary internal applicator.

FIG. 3F shows similar embodiment of internal applicator 301 having insertable part 318 with widened proximal part 316. The widened part of insertable part 316 of internal applicator 301 shown on FIG. 3F may help with keeping the internal applicator inside the body canal or cavity by creating decreased pressure inside the body canal or cavity. The widened proximal part 316 may include at least one energy delivery element 108*a*, however in alternative embodiment may not include no energy delivery element. The distal part 317 may be positioned to distal part of the body canal or cavity (e.g. closer to cervix in vagina) and the widened part 316 may be positioned closer to the labia majora.

The insertable part 318 may include plurality of energy delivery elements 108 (e.g. monopolar, bipolar and/or unipolar electrodes) which may be activated in different manner according to configuration. In one example, all energy delivery elements may be activated simultaneously i.e. in one time segment. In another example one energy delivery element may be activated after another energy delivery element, wherein said energy delivery elements may be located one another or there may be another at least one non-activated energy delivery elements between them. In still another example one group of energy delivery elements (i.e. more than one, e.g. pair) may be activated after another group of energy delivery elements, wherein said groups of energy delivery elements may be located side by side or there may be another at least one non-activated group of energy delivery elements between them. The energy delivery elements may be spaced apart from each other and parallel to each other and perpendicular to the longitudinal axis of the device.

Energy delivery elements may be activated in predetermined order, e.g. all energy delivery elements may be activated in order to simulate movement with the insertable part. In one example, one energy delivery element (e.g. 108a) may be activated and after its active time interval the energy delivery element may deactivated, wherein deactivation of the energy delivery element may be followed by activation of another energy delivery element (e.g. 108b). In another example, one energy delivery element (e.g. 108a) may be activated and another energy delivery element (e.g. 108b) may be activated during active time interval of the energy delivery element (e.g. 108a). Energy delivery elements 108c-f may follow the same logic of activation as energy delivery elements 108a and 108b described previously. In another example, one group of energy delivery elements (e.g. 108a and 108b) may be activated and after active time interval it may be deactivated, wherein deactivation of the group of energy delivery elements may be followed by activation of another group of energy delivery elements (e.g. 108c and 108d). In another example, one group of energy delivery elements (e.g. 108a and 108b) may be activated and another group of energy delivery elements (e.g. 108c and 108d) may be activated during active time interval of the group of energy delivery elements.

The active time interval of one energy delivery element may be in the range of 0.01 second to 120 seconds, more preferably in the range of 0.05 second to 60 seconds, most preferably in the range of 0.01 second to 20 seconds. Also, active time interval of one energy delivery element may be at least 1 or 5 or 10 or 15 or 50 percent different from active time interval of another energy delivery element activated before or after the activation of one energy delivery element. Empty time interval defined as time between deactivation of one energy delivery element and activation of another energy delivery element may be in the range of 0.01 ms to 60 s or 0.05 ms to 30 s or 0.1 ms to 15 s or 0.1 ms to 10 s. Alternatively, empty time interval may be omitted. Length 302 of insertable part may be in the range of 0.5 cm to 25 cm, more preferably in the range of 0.75 cm to 20 cm, even more preferably in the range of 1 cm to 18 cm, most preferably in the range of 1.2 to 18 cm. Also, one or more energy delivery elements may cover the surface of the insertable part in the range of 2% to 100%, more preferably in the range of 5% to 100%, most preferably in the range of 12% to 100% of the surface of the detachable part.

The energy delivery elements 108 (e.g. a monopolar capacitive electrode) are shown as a ring-shaped circular electrodes around or encircling the distal part 317 of the applicator, although it may be also semicircular. It may be part of the distal part 317, and/or proximal part 316 of the insertable part 318. Length of ring-shaped energy delivery elements encircling the applicator may be in the range of 0.1 mm to 100 mm, more preferably in the range of 0.3 mm to 80 mm, even more preferably in the range of 0.5 mm to 60 mm, most preferably in the range of 1 mm to 50 mm. The radius of the ring-shaped circular and/or semicircular energy delivery element 108 may be in the range of 0.1 cm to 25 cm, more preferably in the range of 0.2 cm to 20 cm, even more preferably in the range of 0.4 cm to 15 cm, most preferably in the range of 0.5 cm to 12 cm.

The internal applicator may include at least one temperature sensor 320, e.g. thermocouple, thermistor and a like. Temperature sensor 320 may be embedded inside the wall of the applicator or may be attached to the applicator. The temperature sensor 320 may detect temperature of the energy delivery element and/or temperature of the tissue e.g. epithelium and/or lamina propria. Also the temperature sensor 320 may detect temperature of the volume of the tissue in direct contact with energy delivery element and/or volume of the tissue which is not in direct contact with energy delivery element.

Figure 3G:
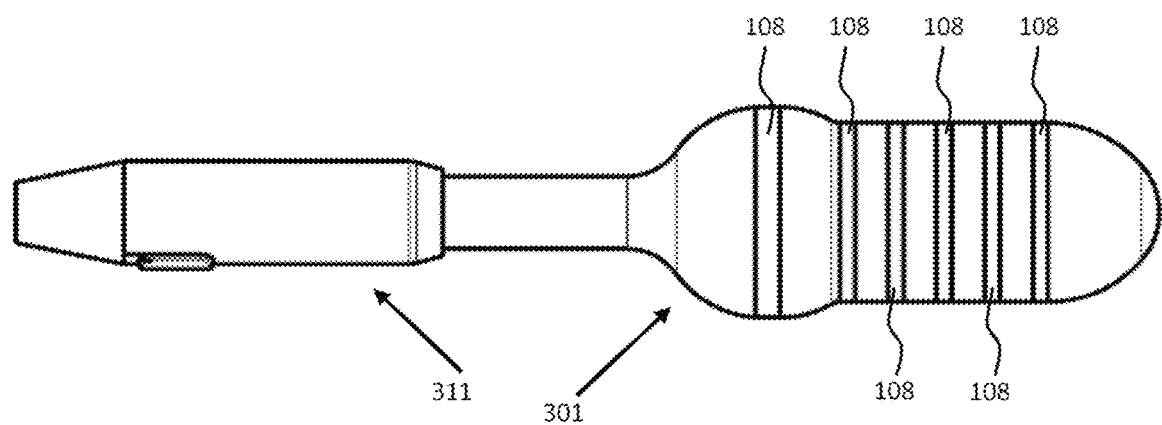
FIG. 3G is an exemplary connection between attaching part and internal applicator in closed configuration.
Figure 3H:
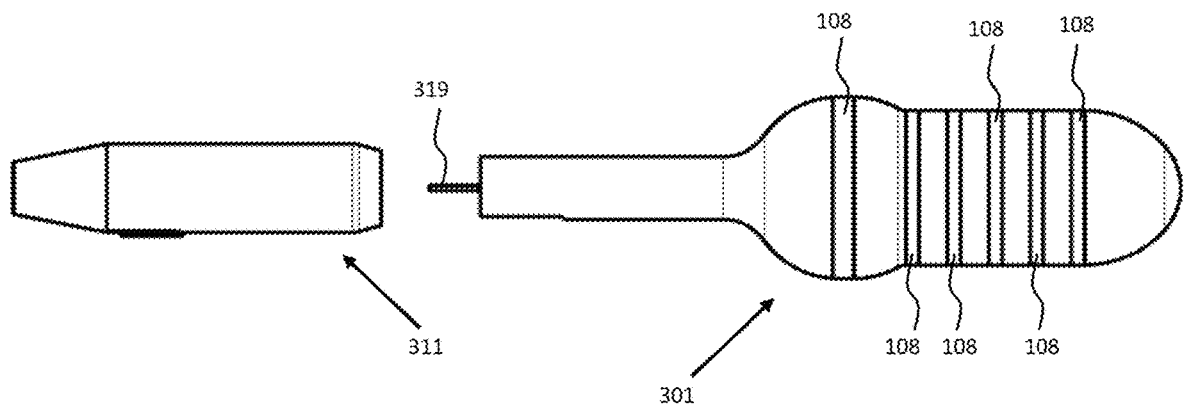
FIG. 3H is another exemplary connection between attaching part and internal applicator in open configuration.
Figure 3I:
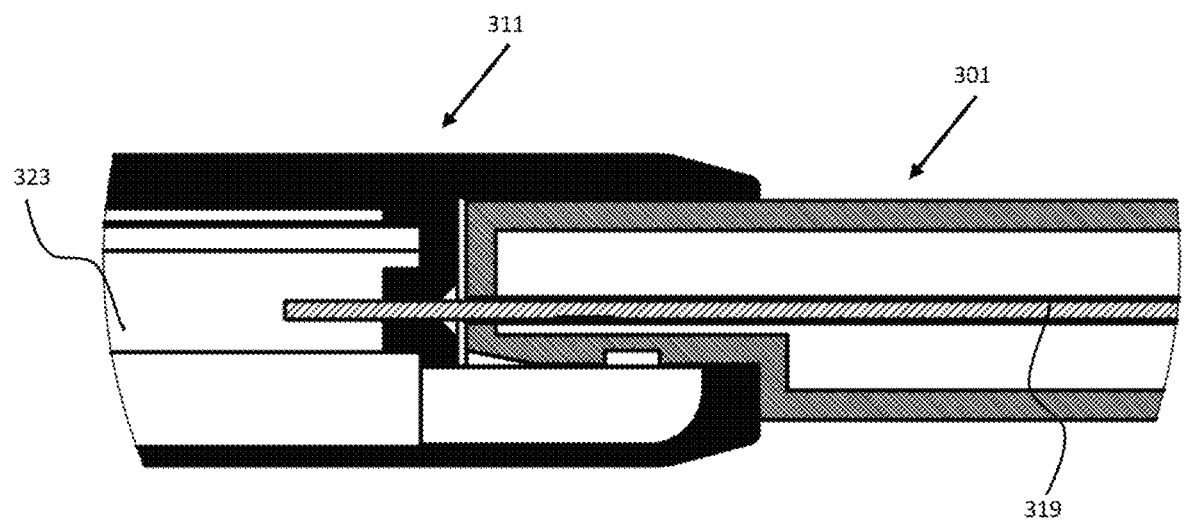
FIG. 3I is an exemplary detailed connection between attaching part and internal applicator in closed configuration.

FIG. 3G show internal applicator 301 as a detachable part couplable to the attaching part 311. FIG. 3H shows internal applicator to be detached from the attaching part 311, which may be integral part of the device and/or also detachable from the device. The internal applicator 301 may be coupled to the attaching part 311 by the male connector 319 shown on the internal applicator. Attaching part 311 may include female connector which may be coupled to the male connector 319 located on the applicator 301. The male connector 319 may be part of or in communication with the printed circuit board located inside of the internal applicator 301, while female connector may be part of and/or be in communication with printed circuit board located in the attaching part 311 or the user interface 104, energy generator 106, central control unit 103 of the device. Also, male connector may be included 319 in the attaching part 311, user interface 104, energy generator 106, central control unit 103 of the device while female connector may be included in the internal applicator 301. The communication between attaching part 311 and the user interface 104, energy generator 106, central control unit 103 and/or device may be provided by wire and/or wirelessly. FIG. 3I shows the exemplary connection of male connector 319 and female connector 323. The male connector 319 may be an edge connector, pin header, insulation-displacement contact or Berg connector.

Insertable part 318, internal applicator 301, patient controller and/or device may include one or more safety elements provide control of activation and/or deactivation of energy delivery element preventing overheating, insufficient heating of the tissue, injury and/or uncomfortable treatment by detecting at least one physical quantity related to delivered energy. Safety element may detect input or output physical quantity of at least one energy/delivery element or all energy delivery elements. When the safety element detects electrical current, the safety element may be e.g. ammeter, shunt resistor, Hall effect current sensor transducer, transformer and/or magnetoresistive field sensor. When the safety element detects voltage, the safety element may be e.g. voltmeter, potentiometer and/or oscilloscope. When the safety element detects electrical resistance and/or electrical conductance, the safety element may be e.g. ohmmeter. When the safety element detects temperature of the energy delivery element, the safety element may be e.g. thermistor, resistance temperature detector, thermocouple, semiconductor-based sensor, infrared sensor and/or thermometer. When the safety element detects electric power, of the energy delivery element, the safety element may be e.g. wattmeter. When the safety element detects light intensity, safety element may be e.g. photometer including at least one photoresistor, photodiode and/or photomultiplier.

Safety element may be coupled to central control unit 103 or energy generator 106 and provide information about function of the device. In one example, when the safety element detects decrease of physical quantity value to 0.5, 1, 3 or 5 percent below predetermined physical quantity value, cease of treatment and/or human perceptible signal (e.g. continuous and/or pulsing colored LEDs, sound signal and/or vibration) may be executed by the device. In one example, when the safety element detects increase of physical quantity value at 0.5, 1, 3 or 5 percent above predetermined physical quantity value, cease of treatment and/or human perceptible signal (e.g. continuous and/or pulsing colored LEDs, sound signal and/or vibration) may be executed by the device.

Device may include plurality of safety energy elements, wherein each safety element may detect physical quantity related to each of the plurality of energy delivery elements. Safety element may be located on the printed circuit board, which may be located inside the insertable part 318.

The internal applicator may also include one or more rotational apparatus, which may provide rotational movement to the applicator and/or its parts. The present methods and devices may use rotational movement to provide treatment to the whole surface of the cavity and/or canal without any manually challenging movement by the operator. This may lead to reduced/movement of the applicator. One or more detachable parts 308 or the internal applicator 301 may be rotated around a longitudinal axis, or. the whole internal applicator may be rotated around its longitudinal axis. Optionally, one of complementary electrodes of the bipolar pair may be rotated.

Figure 4A:
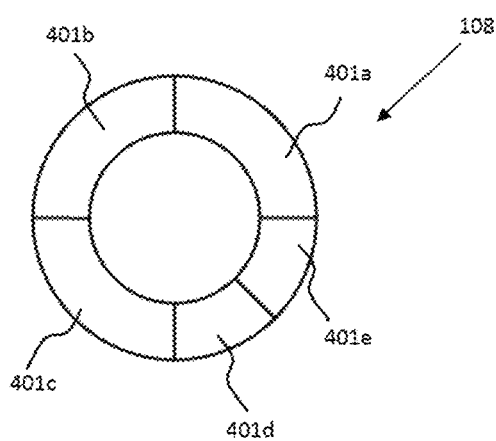
FIG. 4A is an exemplary view of the energy delivery element
Figure 4B:
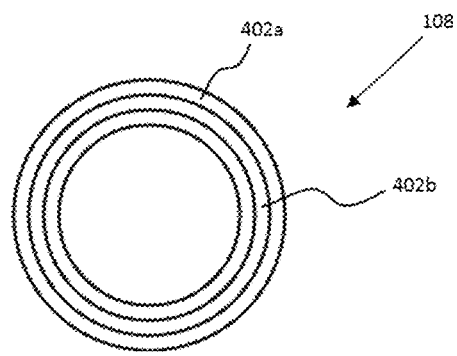
FIG. 4B is another exemplary view of the energy delivery element

FIG. 4A shows a ring-shaped circular energy delivery element 108 divided to segments 401*a*-401*e*. Energy delivery element 108 may be divided to at least two, three, four or more than four arcs similar to the segments 401*a*-401*e*. Angular sections of the segment 401 (e.g. 401*a*) may be in the range of 1° to 359° or 5° to 275° to 15° to 185° or 20° to 95°. Arcs 401*a* and 401*b* may transfer energy to upper part of tissue (e.g. vagina), while the other segments are deactivated. Other segments may be activated after the ceasing operation of segments 401*a*-*b* and/or during the operation of segments 401*a*-*b*. Segments 401*a*-*e* may be independently controlled in order to deliver the energy to close parts of the tissue. In FIG. 4B the energy delivery element 108 is divided into one or more layers. At least part of the energy delivery element may be divided into at least two layers as represented by layers 402*a* and 402*b*. Optionally, one or more segments 401*a*-*e* may be divided into layers 402*a*-*b*. Segments 401*a*-401*e* and layers 402*a*-*b* may be detachable from the applicator and act as a detachable element 308. Additionally, the energy delivery element 108 may encircle only part of the applicator.

The internal applicator may include a shield member 314 protecting a urethral orifice and/or urethra. Such shield member may provide decreased occurrence of adverse events including e.g. urinary tract infection. It may be e.g. plastic cover on one side surface of the insertable part of the applicator. Optionally it may be a membrane plug and/or membrane surface covering the urethra during the treatment. It may also be an additional energy delivery element positioned closely to the urethral orifice devoted to apply such type and/or of energy to tighten the urethra during the treatment. As already mentioned, the energy delivery element may form the ring-shaped circular or semicircular shape. The shield member may therefore be a complement to the semicircular energy delivery element. Thus, the shield member and energy delivery element may create joint circular shape resembling the circular energy delivery element shown on FIG. 2. In such case, the energy delivery element may form the at least 45%, more preferably 55%, even more preferably 65%, most preferably 80% of the joint circular shape.

The internal applicator 301 may also be distanced from the tissue by a spacing object. In such configuration, the thickness of the spacing object may be in the range of 0.01 cm to 2 cm, more preferably in the range of 0.03 cm to 1.5 cm, even more preferably in the range of 0.05 cm to 1.25 cm, most preferably in the range of 0.1 cm to 1 cm. The spacing object may be filled with fluid, e.g. water, silicone, ethylene glycol, polymer fibres, carbon dioxide and/or air.

Optionally, the applicator may be in a form of a thin structure e.g. a flexible structure containing an energy delivery element inserted into the tissue in the rolled form, where it may be unrolled.

Figure 5A:
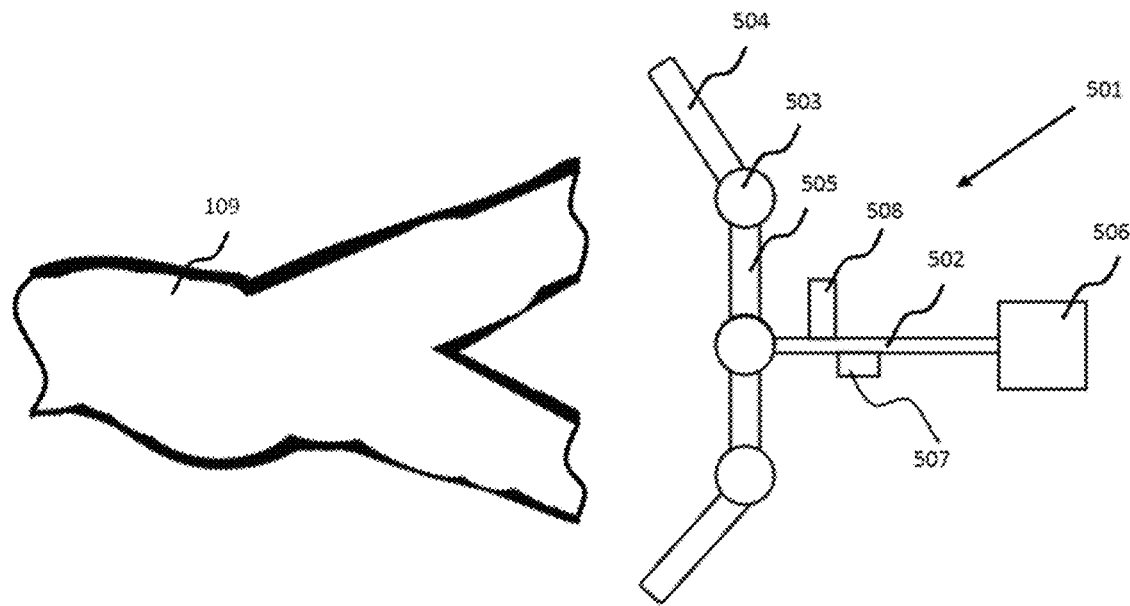
FIG. 5A is a view of an exemplary external applicator.

The external applicator may be positioned above the tissue which may include female genital tissue and/or its surrounding external tissue. FIG. 5A illustrates the external applicator 501 not contacting the tissue 109. The applicator may be positioned by one or more mechanical arms 502 and/or by hand. Joints 503 may adjust shape and/or position of external applicator 501 by movement of one or more adjustable elements, e.g. outer adjustable element 504 and/or inner adjustable element 505. The external applicator may also include only one adjustable element. Adjustable elements and/or joints 503 may contain energy delivery elements, sensors. One and more adjustable elements and/or joints may be detachable.

One and more parts of the external applicator and/or mechanical arm may contain and/or be attached to a motor unit 506 providing movement. Optionally, one or more portions of the device may be moved manually. The applicator may be moveable in one or more axis of Cartesian coordinate system. Movement may be represented by rotation, tilting and/or translation movement of portions of the device. The movement may provide sufficient adaptation of the applicator to the anatomy of the human body. Inner adjustable elements 505 and/or outer adjustable elements 504 may be tilted to be positioned adjacent to the treated tissue.

The position of the device and/or its parts may be tracked by a sensor 507 for obtaining feedback. The sensor may be an inclinometer, an accelerometer, a load cell, a force sensor, a magnetic sensor, a distance sensor and/or an optic sensor.

The external applicator and/or one or more its parts may be positioned in a static position or it may be moved during treatment. Portions of the device may be moved and repeatedly stopped in predetermined positions during treatment. The static position in the predetermined position may be provided by a locking mechanism 508. The locking mechanism may be mechanical e.g. latching member, screw mechanism, self-locking mechanism such as worm gearing, electromagnetic and/or magnetic e.g. electromagnetic brake.

The external applicator 501 may be distanced from the tissue by a gap. The gap may be an air gap, or a fluid gap which may change the characteristic of the transferred energy, e.g. it may provide inhibition of electric energy and/or magnetic energy of electromagnetic radiation. Adjustable parts and/or joints may include nozzles and/or other known technical solutions speeding air circulation through the gap in the vicinity of the tissue. Air circulation may provide cooling effects together with control of perspiration. Other kinds of fluid e.g. water vapor, inert gases (e.g. noble gases, nitrogen) and carbon dioxide may also be used. The thickness of the gap may be in the range of 0.01 cm to 50 cm, more preferably in the range of 0.03 cm to 35 cm, even more preferably in the range of 0.05 cm to 30 cm, most preferably in the range of 0.1 cm to 25 cm. Thickness of the gap may be constant or variable during the treatment.

The external applicator 501 may also be distanced from the tissue by a spacing object. In such configuration, the thickness of the spacing object may be in the range of 0.01 cm to 50 cm, more preferably in the range of 0.03 cm to 35 cm, even more preferably in the range of 0.05 cm to 30 cm, most preferably in the range of 0.1 cm to 25 cm. The spacing object may be filled with fluid, e.g. water, silicone, polymer fibres and/or fluids mentioned above.

Figure 5B:
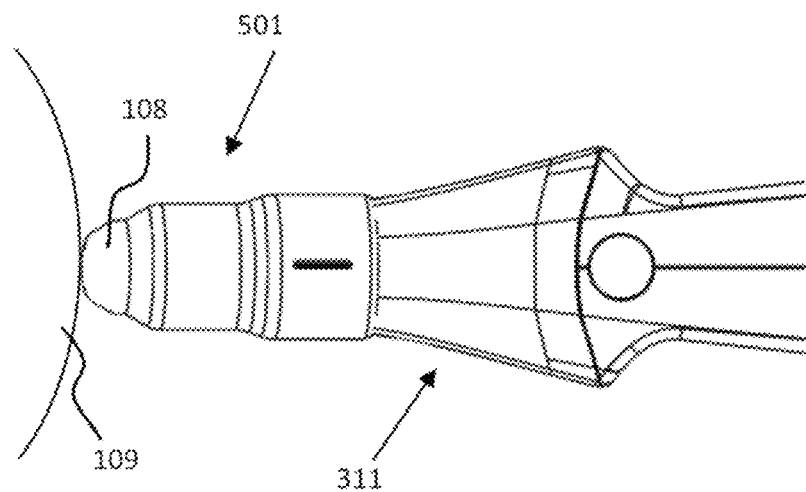
FIG. 5B is another view of an exemplary external applicator.

FIG. 5B shows an external applicator 501 attached to a part of a device through an attaching part 311. Energy delivery element 108 is shown in contact with tissue 109. The conical-shape of the external applicator shown in FIG. 5B may provide smooth and soft treatment. The length of the energy delivery element of the applicator may be in the range of 0.01 cm to 25 cm, more preferably 0.05 cm to 20 cm, even more preferably 0.1 cm to 17 cm, most preferably 0.2 cm to 15 cm.

The external applicator may also have shape of an undergarment, sanitary napkin, panties, C-string, diaper and/or trousers, with the external applicator worn during common activities.

The external applicator may treat a patient without the necessity of removing the underwear and/or clothes. All types of applicators may be incorporated into support structures (e.g. bed or chair).

The methods of treatment are performed by the operator i.e. the patient or a medical professional such as a doctor, nurse or technician. Such treatment may be done at home, at beauty salon and/or in a hospital. Generally, a medical professional is not needed and the treatment may be characterized by executing the method and applying the energy under the control of the patient e.g. by strictly manual movement of the applicator.

The methods and devices may be self-operated. Self-operated treatment may be characterized by the initial manual configuration of the device followed by automated and/or corrected treatment of the tissue. Optionally, self-operated treatment may be performed without initial manual configuration. In this case, the system may set all the parameters according to its calibration.

The method and device may include automatic feedback based on information from one and more sensors measuring e.g. temperature, impedance, phase angle of reflected energy, phase angle of delivered energy and/or pressure. The feedback may include the slowing and/or ceasing of penetration of the device into the cavities and/or canals (e.g. vulvar vestibule and/or vagina), change of pressure in the expandable element, change of energy characteristics (frequency, power output), change of treatment time and temperature of the device. Additionally, feedback may include activation and/or deactivation of at least one energy delivery element delivering different type of energy (e.g. plasma, mechanical energy).

Methods of treatment may include initial configuration, treatment and discontinuation. These phases of the method may follow the disclosed order or their order may be changed. Also, there may be more than one of the same phase used during a method of treatment. Such situations may occur for example when the treatment is interrupted by a discontinuation and later the treatment continues. Also, the method of treatment may not include all phases of treatment.

The initial configuration may include assembling of the applicator, the setting of the initial position of the applicator, one or more portion of the applicator, type of energy, one or more characteristics of the energy, type of first and second energy, desired temperature of the tissue, volume of fluid in the spacing object, volume of fluid in the expendable element, pressure in the spacing object, pressure in the expendable element, position of at least one energy delivery element, rotational velocity of the applicator, velocity of translational movement of the applicator and/or one or more its portions. Following treatment may include the change of all characteristics which are mentioned in relation to the initial configuration.

Assembling of the applicator may include connecting the internal applicator 301 to the device and/or connecting the internal applicator 301 to the attaching part 311 e.g. through male and/or female connector wherein the attaching part 311 may be then connected or be already connected to the rest of the device.

Concerning the initial location, the device and method including the internal applicator 301 (shown on FIGS. 3A-3F) may be manually inserted into a cavity and/or canal, e.g. vulvar vestibule and/or vagina. The internal applicator 301 may be positioned just in the vaginal opening, between labia majora and cervix, between labia minora and cervix, in the approximate center of the vaginal canal, on the vaginal cervix and/or any other place between these locations. The applicator may be positioned before the delivery of energy or during the delivery of energy. The applicator may be positioned onto or into the tissue.

Figure 5C:
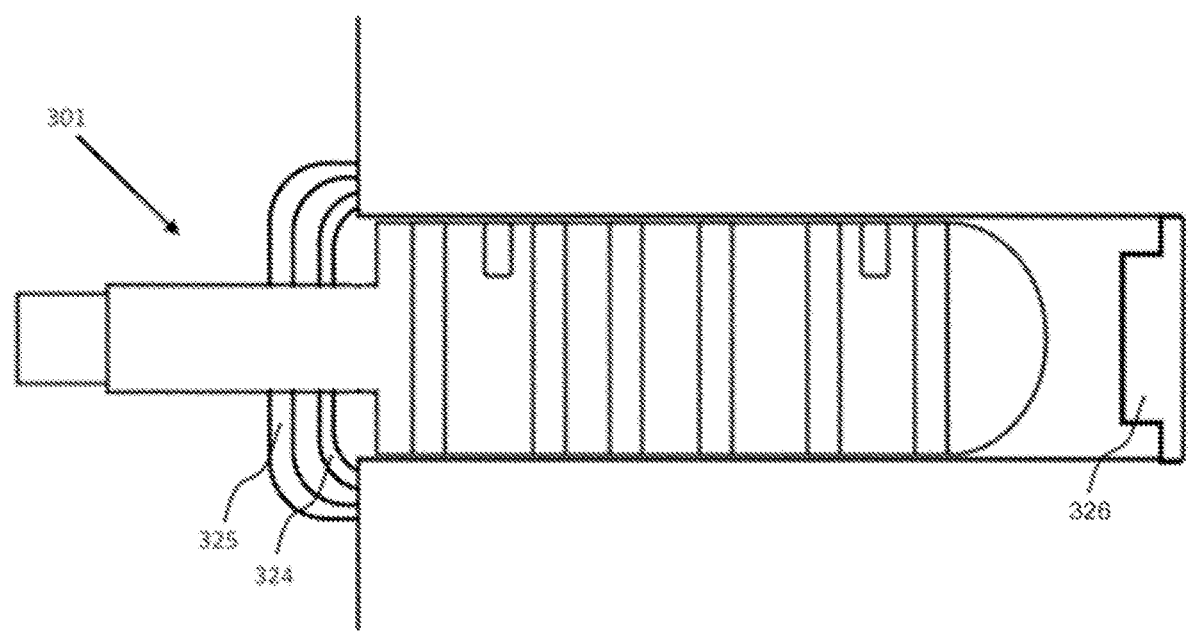
FIG. 5C is an exemplary representation of the internal applicator including insertable part positioned in the vagina.

When the applicator includes insertable part 318 which may be inserted into body canal and/or cavity, it may be inserted into depth of at least 0.5 cm or 1 cm or 1.5 and no more than 30 cm or 25 cm or 20 cm. When positioned into vagina, the insertable part 318 may be positioned between labia majora and cervix, between labia minora and cervix and/or between vaginal opening and cervix. The insertable part may be positioned onto or into the tissue. Widened proximal part (shown on FIG. 3F as element 316) may be positioned between labia majora and cervix, between labia minora and cervix, in proximity of vaginal opening and/or between vaginal opening and cervix. and/or in contact with the vaginal opening. Connection of connectors of attaching part 311 and internal applicator 301 may be during setting initial positions and/or treatment positioned before labia majora and/or labia minora. FIG. 5C shows internal applicator 301 including insertable part positioned in the vagina between vaginal opening and cervix 326 while the connection of attaching part 311 and internal applicator 301 is positioned before labia majora 325 and labia minora 324

After the initial configuration and during treatment, the applicator may be left in the desired position or it may be continually or intermittently moved manually or in an automatic mode from one position to another providing energy to the tissue. Insertable part of the applicators shown on FIGS. 3E and 3F may be positioned into body canal and/or cavity before treatment or delivery of energy. During the treatment or delivery of energy, insertable part may not be moved a may be lift in original position in the body canal and/or cavity. The initial location of the device including the applicator may alternatively be positioned adjacent to the tissue. The applicator may be in the direct contact with the tissue. External applicator may be initially set to be located above the tissue (applicator shown on FIG. 5A) or in contact with the tissue (FIG. 5B). After the initial configuration the external applicator and/or at least one of its portions may be inclined and/or inclined during the treatment, and the external applicator may move adjacent to the tissue.

During the treatment the at least one energy delivery element of the applicator may be activated and the applicator may be continually or intermittently moved manually or in an automatic mode from one position to another providing energy to the tissue.

Internal applicator 301 may include or be connected to the linear actuator or motor for movement during treatment, wherein movement may include rotation and/or linear movement. Internal applicator 301 may be coupled to patient by an adhesive member (e.g. band), bandage, or by including an internal applicator 301 as a part of a garment (e.g. undergarment, sanitary napkin, panties, C-string, diaper and/or trousers).

When the applicator includes plurality of energy delivery elements (e.g. applicator shown on FIG. 3E or 3F), activation of energy delivery element may simulate the movement with the insertable part of the applicator. In one example shown on 3AE the activation of energy delivery element 108a may be followed by subsequent activation of energy delivery element 108b and subsequent application of other energy delivery elements 108b-108f, as marked by arrow representing forward direction 321. After the activation of energy delivery elements in one direction, activation of same energy delivery elements in backward direction 322 from energy delivery element 108f back to 108a may occur. It may be possible to change the order of direction of activation, such that firstly the energy delivery element may be activated in backward direction 322 and then in forward direction 321. In another example different energy delivery element different than 108a may be activated first and activation of other energy delivery elements in forward direction 321 or backward direction 322 may occur.

Figure 6A:
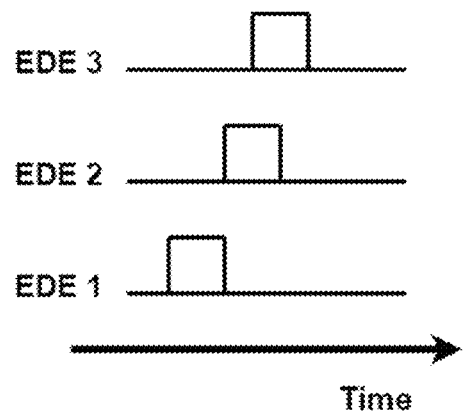
FIG. 6A is an exemplary operation scheme of the activation of energy delivery elements.
Figure 6B:
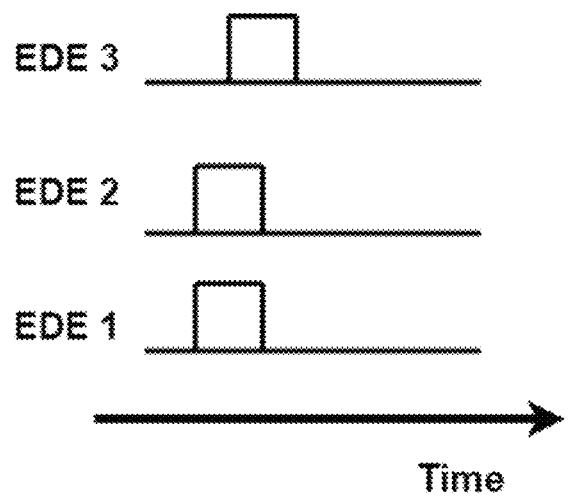
FIG. 6B is another exemplary operation scheme of the activation of energy delivery elements.
Figure 6C:
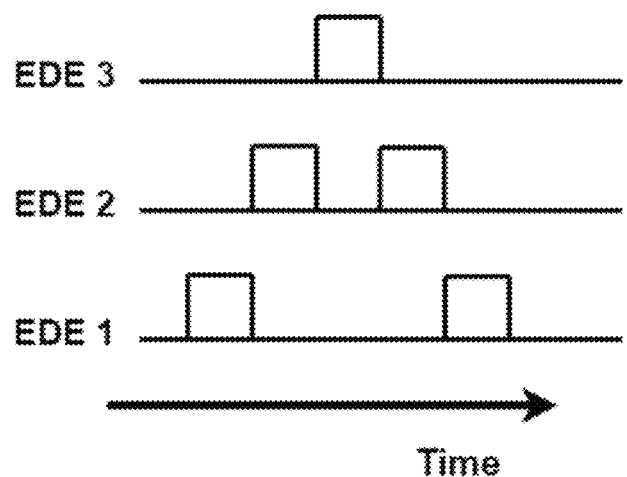
FIG. 6C is another exemplary operation scheme of the activation of energy delivery elements.

FIGS. 6A-D shows various exemplary embodiments of operation scheme of plurality of energy delivery elements (marked as EDE, preferably electrodes delivering radiofrequency) during treatment. Boxes on each line representing the time operation of the energy delivery element represents active operation of the energy delivery element. FIG. 6A shows exemplary operation scheme where the second energy delivery element may be activated after the activation and deactivation of first energy delivery element. Third energy delivery element may be activated during when the second energy delivery element may be still active. FIG. 6B shows another exemplary operation scheme where the first and second energy delivery elements may be activated in same time and third energy delivery element may be activated when first and second energy delivery element may be still active. FIG. 6C shows another exemplary operation scheme where the plurality of energy element may be activated one after another followed with backward activation. Show operation scheme represents an example according to forward direction 321 followed by backward direction 322 as shown on FIG. 3E.

Figure 6D:
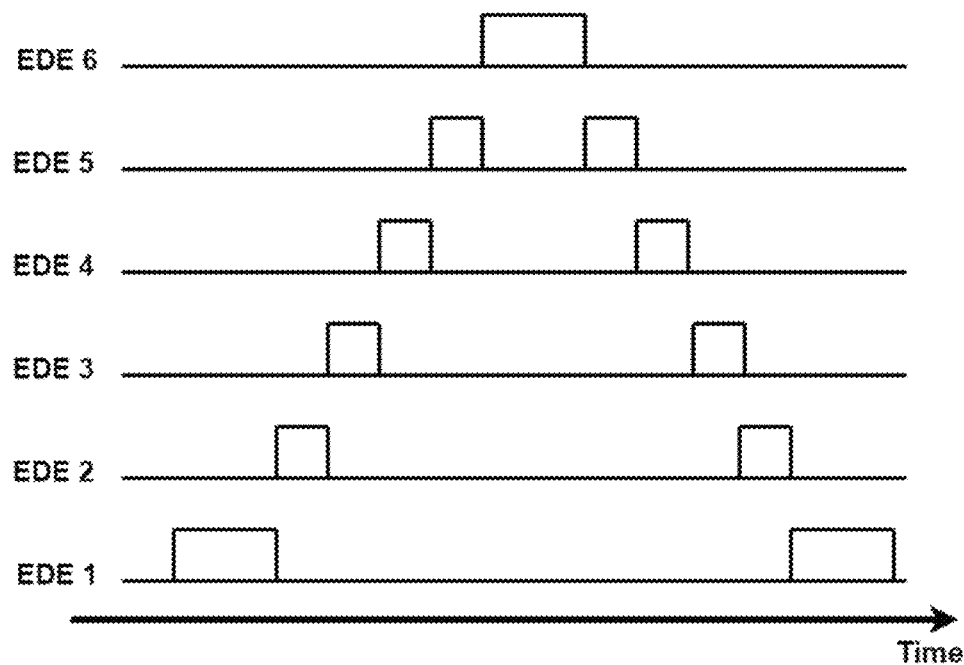
FIG. 6D is another exemplary operation scheme of the activation of energy delivery elements.

FIG. 6D shows another exemplary embodiment of applicator including six energy delivery elements and different active time intervals for first and sixth electrode. Plurality of energy delivery elements may be activated one after another without any empty time interval between activation of another energy delivery element. Active time interval for first and sixth energy delivery element may be at longer than active time interval of another energy delivery element. In preferred example, the active time interval of the first and sixth energy delivery elements may be twice as long as the active time interval of another energy delivery element.

Figure 7A:
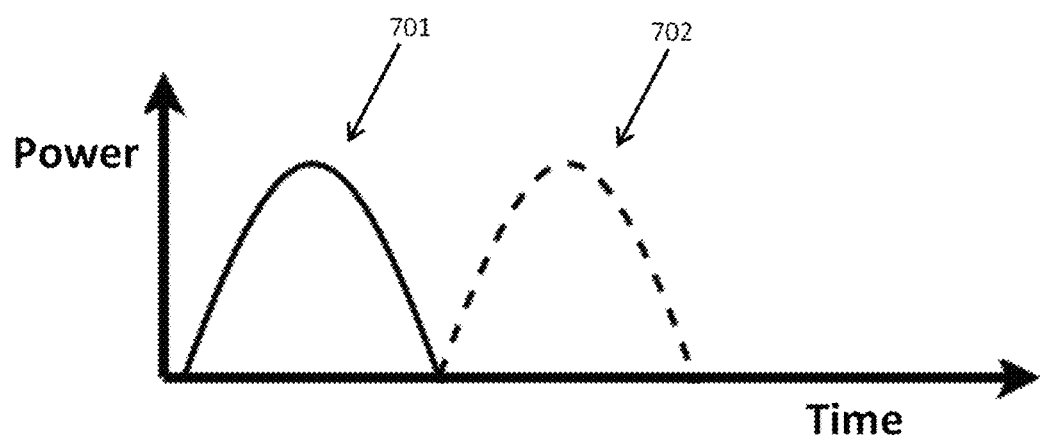
FIG. 7A is an exemplary power distribution layout of active energy delivery elements.

The FIGS. 7A-D shows exemplary power distribution layout of plurality e.g. at least two energy delivery elements. The power distribution may represent the power of energy delivered by one energy delivery element. The power distribution of the active energy delivery amplitudes may vary in time in order to simulate the movement of the insertable part. FIG. 7A shows exemplary layout where the power distribution 701 of one active energy delivery element may be followed by power distribution 702 of another active energy delivery element. The situation may correspond to situation shown on FIG. 6A for EDE1 and EDE2. As both power distributions are same in amplitude, the energy delivered by one and another active energy delivery element may be the same. Also, one active energy delivery element may be activated and deliver the energy with the power amplitude 701 and after the deactivation of the active energy delivery element, another active energy delivery element may be activated and deliver the energy with the power amplitude 702.

Figure 7B:
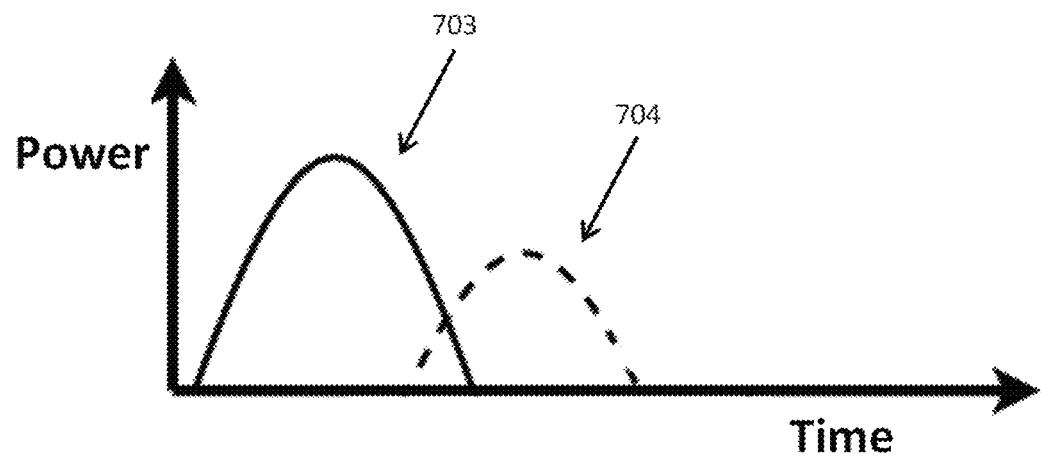
FIG. 7B is another exemplary power distribution layout of active energy delivery elements.
Figure 7C:
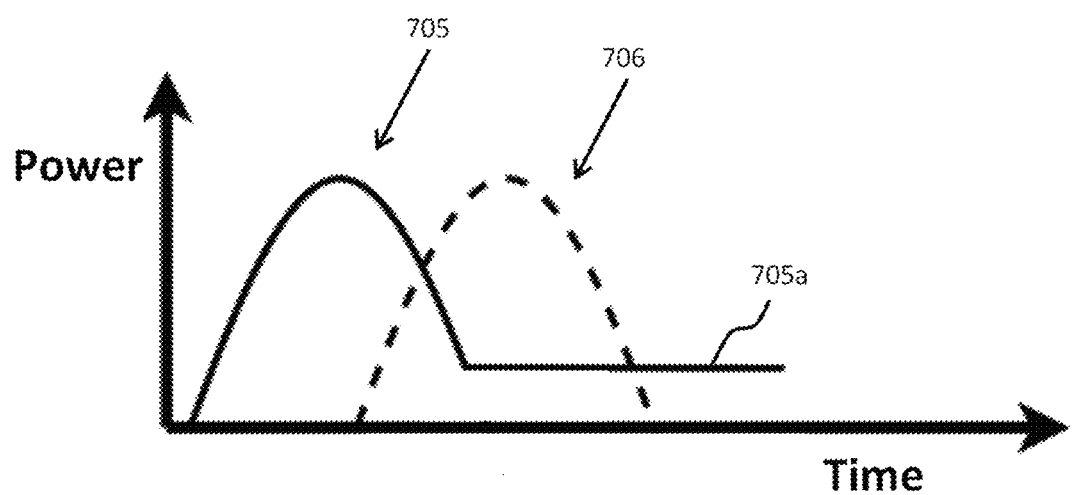
FIG. 7C is another exemplary power distribution layout of active energy delivery elements.
Figure 7D:
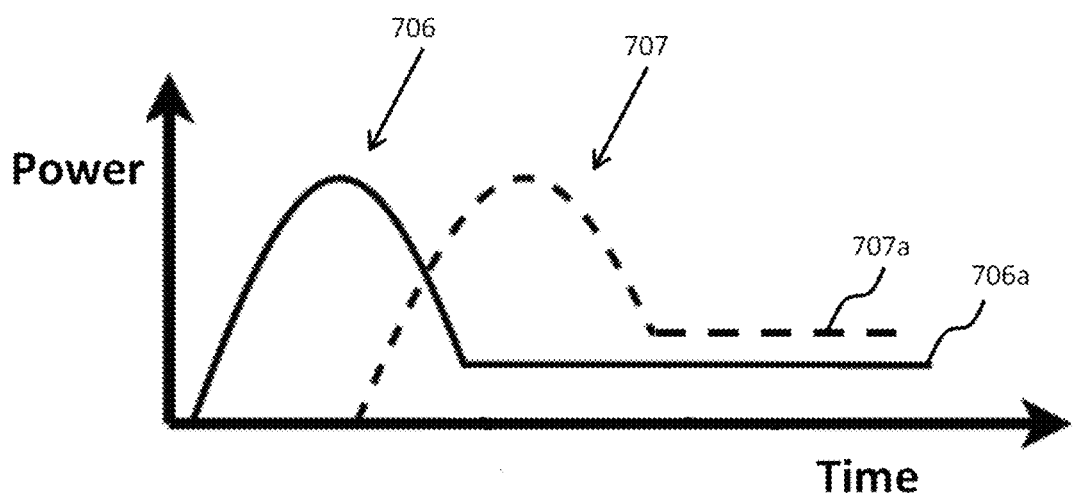
FIG. 7D is another exemplary power distribution layout of active energy delivery elements.

FIG. 7B shows another exemplary layout where the power distribution 703 of one energy delivery element may be followed by power distribution 704 of another energy delivery element, wherein the power distribution 704 may start during the power distribution 703. Also, the power amplitude of power distribution 703 representing energy delivered by one active energy delivery element may be higher than power distribution 704 representing energy delivered by another active energy delivery element. The FIG. 7C shows another exemplary layout where the power distribution 705 of one active energy delivery element may be followed by power distribution 706 of another active energy delivery element. Power distribution 705 may include power amplitude and phase with constant power, wherein the constant power may be predetermined by operator and/or central control unit 103. Another energy delivery element providing power distribution 706 may be activated before and/or during the constant phase of the power distribution 705. The FIG. 7D shows another exemplary layout where the power distribution 707 of one active energy delivery element may be followed by power distribution 708 of another active energy delivery element. Both power distributions 707 and 708 may include power amplitude and phase with constant power, wherein the constant power may be predetermined by operator and/or central control unit 103 and maybe different for each power distribution. Another energy delivery element providing power distribution 708 may be activated before and/or during the constant phase of the power distribution 707. Constant phase of the power distribution may be provided before and/or after the power amplitude. Constant phase of the power distribution may be constant at about 10 or 15 or 20 or 25 or 30 percent of maximal power output of the energy.

The applicator may be initially configured to apply electromagnetic energy (e.g. light, radiofrequency energy and/or microwave energy). During the treatment the application of electromagnetic energy (including light, radiofrequency energy and microwave energy) may be replaced with the application of mechanical energy (including ultrasound energy and shock wave energy), electric energy, thermal energy, magnetic energy and/or plasma. Treatment may require different energy type, depth, power focus. The frequency and/or power may be changed during treatment. Some of the energy replacement may also lead to a change of depth of treatment and/or focusing of the energy. The application of the mechanical energy (e.g. ultrasound and/or shock wave energy) may lead to creation of focus at a desired depth of the tissue and/or defocusing the energy into a larger area of the tissue. However, any other kind of energy may be provided in focused, nonfocused or a defocused manner.

The internal applicator 301 may be initially inserted into a canal e.g. vagina, and then perform automated rotational and/or linear movement to treat the tissue.

One and more characteristics (e.g. temperature of the tissue, temperature of the energy delivery element, pressure etc.) of the treatment may be checked by at least one sensor before, during and/or after treatment and processed by the device. Processed information demanding awareness (e.g. loss of contact of the applicator with the tissue) may be signaled by any human perceptible signal (e.g. continuous and/or pulsing colored LEDs, sound signal and/or vibration).

Optionally, the at least one characteristic and/or parameter may be corrected by the device. The parameter measured by sensor may be impedance, phase angle, contact, temperature, flux density and the like.

The sensor and/or operator may determine the friction and/or humidity of the tissue. In this case, the device may provide a human perceptible signal to inform the operator about the necessity of supplying the fluid and/or induce the reservoir to release an amount of fluid.

Discontinuation may be temporary and permanent. Permanent discontinuation may occur at the end of the treatment. Temporary discontinuation may include cease of operation commanded by safety element and/or central control unit 103.

All parameters and characteristics of the treatment with respect to self-operated treatment may be corrected by the patient and/or operator.

The method and device may provide controlled local treatment of the tissue. The device may provide information about the tissue to be treated. For example, the anal canal, vaginal canal and/or external part of the genitalia may be divided into sectors, where the sectors to be treated may be identified by a sensor. The treatment may then aim at least one of these sectors according to its severity e.g. laxity.

The energy generator 106 and/or energy delivery element providing RF energy may include or cooperate with a transmatch and/or a balancing/unbalancing element (e.g. balun), wherein at least one of the transmatch and/or balancing/unbalancing element is regulated by a control unit or e.g. by an SWR meter in order to tune power, phase, impedance and or amplitude of the RF energy.

The foregoing description of preferred embodiments has been presented for purposes of illustration and description. It is not intended to be exhaustive or to limit the invention to the precise form disclosed. Modification and variations are possible in light of the above teachings or may be acquired from practice of the invention. All mentioned embodiments may be combined. The embodiments described explain the principles of the invention and its practical application to enable one skilled in the art to utilize the invention. Various modifications as are suited to a particular use are contemplated. It is intended that the scope of the invention be defined by the claims appended hereto and their equivalents.

LIST OF ELEMENTS 101 power supply
102 emergency stop button
103 central control unit
104 user interface
105 applicator
106 energy generator
107 casing
108 energy delivery element
109 tissue
110 cooling and heating system
111 storage tank
112 sensor
113 spacing object
201 circle
202 disc
203 strips
204 strips
205 triangular elements
206 healing element
301 internal applicator
302 length
303 distal part of applicator
304 proximal part
305 curvature
306 smaller mark
307 bigger mark
308 detachable part
310 expandable element
311 attaching part
312 nozzle
313 proximity sensor
314 shield member
315 non-insertable part
316 proximal part
317 distal part
318 insertable part
319 male connector
320 temperature sensor
321 forward direction
322 backward direction
323 female connector
324 labia minora
325 labia majora

We claim:

1. A method for a female genital tissue treatment comprising:
   providing an internal applicator including an insertable part and a non-insertable part;
   assembling the insertable part with first and second detachable parts along a length of the insertable part, wherein the first detachable part includes a first ring-shaped circular radiofrequency electrode encircling or around the first detachable part and the second detachable part includes a second ring-shaped circular radiofrequency electrode encircling or around the second detachable part;
   with the first and second ring-shaped circular radiofrequency electrodes having a length in a range of 0.1 mm to 100 mm and a radius in a range of 0.2 cm to 20 cm;
   wherein the non-insertable part, the first and second detachable parts and centers of the first and second ring-shaped circular radiofrequency electrodes are configured to be on the same longitudinal axis;
   wherein the first and second ring-shaped circular radiofrequency electrodes are perpendicular to the longitudinal axis; and
   wherein the first and the second ring-shaped circular radiofrequency electrodes are spaced apart from each other by a distance in a range of 0.01 mm to 20 mm;

inserting the insertable part having a length in a range of 0.75 cm to 20 cm at east partially into a vagina;

transferring a radiofrequency energy into the genital tissue of the vagina with the first and second ring-shaped circular radiofrequency electrodes;

wherein the radiofrequency energy is in a range of 350 kHz to 100 MHz with an output up to 450 W providing an energy flux in a range 0.001 W/cm$^2$ to 1500 W/cm$^2$; and heating an epithelium of the vagina.

2. The method of claim 1, wherein the first and second ring-shaped circular radiofrequency electrodes cover 2% to 100% of the surface of the insertable part.

3. The method of claim 1, wherein the insertable part is positioned between a labia minora and a cervix.

4. The method of claim 1, further including generating the radiofrequency energy by the first ring-shaped circular radiofrequency electrode for a first active time interval and generating the radiofrequency energy by the second ring-shaped circular radiofrequency electrode for a second active time interval, wherein the second active time interval is in a range of 0.05 seconds to 60 seconds, and wherein the second active time interval begins after a beginning of the first active time interval.

5. The method of claim 4, wherein the second active time interval begins during the first active time interval.

6. The method of claim 4, wherein the second active time interval is at east 5 percent longer than the first active time interval or vice versa.

7. A method for a female genital tissue treatment comprising:

providing an internal applicator including an insertable part and a non-insertable part;

wherein the insertable part includes a first ring-shaped circular electrode and a second electrode;

wherein the first ring-shaped circular electrode is configured to provide a radiofrequency energy and the second electrode is configured to provide an electric energy different from the radiofrequency energy;

with the first ring-shaped circular electrode and the second electrode having a length in a range of 0.1 mm to 100 mm and a radius in a range of 0.2 cm to 20 cm;

wherein the non-insertable part and a center of at least one of the first ring-shaped circular electrode or the second electrode are configured to be on a same longitudinal axis;

wherein the first ring-shaped circular electrode and the second electrode are perpendicular to the longitudinal axis; and wherein the first ring-shaped circular electrode and the second electrode are spaced apart from each other by a distance in a range of 001 mm to 20 mm;

inserting the insertable part having a length in a range of 0.75 cm to 20 cm at least partially into a vagina;

transferring the radiofrequency energy into the genital tissue of the vagina with the first ring-shaped circular electrode to heat an epithelium of the vagina to a temperature in a range of 35° C. to 48° C.;

wherein the radiofrequency energy is in a range of 350 kHz to 100 MHz with an output up to 450 W providing an energy flux in a range 0.001 W/cm$^2$ to 1500 W/cm$^2$; and transferring the electric energy into the genital tissue of the vagina with the second electrode to cause muscle stimulation b the electric energy;

wherein the electric energy is applied in pulses in a range of 0.05 Hz to 85 Hz.

8. The method of claim 7, further including applying the radiofrequency energy and the electric energy simultaneously.

9. The method of claim 7, further including applying the radiofrequency energy and the electric energy in at least partial overlap.

10. The method of claim 7, wherein the insertable part comprises at least one sensor configured to communicate with a control unit.

11. The method of claim 10, wherein the at least one sensor is a temperature sensor.

12. The method of claim 7, wherein the muscle stimulation caused by applying the electric energy is a muscle contraction.

13. The method of claim 7, wherein the temperature of heating the epithelium of the vagina with the radiofrequency energy is in the range of 40.5° C. to 43.5° C.

14. A method for a female genital tissue treatment comprising:

providing an internal applicator including an insertable part and a non-insertable part;

wherein the insertable part includes a first energy delivery element and a second energy delivery element configured for treatment of a vaginal tissue;

wherein the first energy delivery element is a first ring-shaped circular electrode;

wherein the first ring-shaped circular electrode is configured to provide a radiofrequency energy and the second energy delivery element is configured to provide an electric energy different from the radiofrequency energy;

with the first ring-shaped circular electrode having a length in a range of 0.1 mm to 100 mm and a radius in a range of 0.2 cm to 20 cm;

wherein the non-insertable part and a center of at least one of the first ring-shaped circular electrode or the second energy delivery element are configured to be on a same longitudinal axis;

wherein the first ring-shaped circular electrode and the second energy delivery element are perpendicular to the longitudinal axis; and wherein the first ring-shaped circular electrode and the second energy delivery element are spaced apart from each other by a distance in a range of 0.01 mm to 20 mm;

inserting the insertable part having a length in a range of 0.75 cm to 20 cm at least partially into a vagina;

transferring the radiofrequency energy into the genital tissue of the vagina with the first ring-shaped circular electrode to heat an epithelium of the vagina;

wherein the radiofrequency energy is in a range of 350 kHz to 100 MHz with an output up to 450 W providing an energy flux in a range 0.001 W/cm$^2$ to 1500 W/cm$^2$; and transferring the electric energy into the genital tissue of the vagina with the second electrode;

wherein the electric energy is configured to provide a nonthermal effect.

15. The method of claim 14, wherein the second energy delivery element is a second ring-shaped circular electrode.

16. The method of claim 14, wherein the temperature of heating the epithelium of the vagina with the radiofrequency energy is in a range of 40.5° C. to 43.5° C.

17. The method of claim 14, further providing maintaining a stability of vaginal laxity.

18. The method of claim 14, further comprising delivering the energy to a patient in a self-operated manner without continuous supervision or manual action of an operator.

19. The method of claim 14, wherein the first energy delivery element or the second energy delivery element is divided into segments.

20. The method of claim 14, wherein the nonthermal effect is one of muscle stimulation, analgesic effect, contraction of muscles and/or myorelaxation effect.

* * * * *